(12) United States Patent
Mason et al.

(10) Patent No.: US 12,220,202 B2
(45) Date of Patent: *Feb. 11, 2025

(54) REMOTE EXAMINATION THROUGH AUGMENTED REALITY

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM Technologies, Inc., Brookfield, CT (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/684,309

(22) Filed: Mar. 1, 2022

(65) Prior Publication Data

US 2022/0183557 A1  Jun. 16, 2022

Related U.S. Application Data

(63) Continuation of application No. 17/379,533, filed on Jul. 19, 2021, now Pat. No. 11,284,797, which is a
(Continued)

(51) Int. Cl.
*A61B 5/00* (2006.01)
*A61B 5/15* (2006.01)
*G16H 40/67* (2018.01)

(52) U.S. Cl.
CPC .......... *A61B 5/0022* (2013.01); *A61B 5/0008* (2013.01); *A61B 5/150954* (2013.01); *A61B 5/744* (2013.01); *G16H 40/67* (2018.01)

(58) Field of Classification Search
CPC ................ A61B 5/0008; A61B 5/0022; A61B 5/150954; A61B 5/221; A61B 5/744;
(Continued)

(56) References Cited

U.S. PATENT DOCUMENTS

| 823,712 A | 6/1906 | Uhlmann |
| 4,499,900 A | 2/1985 | Petrofsky et al. |

(Continued)

FOREIGN PATENT DOCUMENTS

| CA | 3193419 A1 | 3/2022 |
| CN | 2885238 Y | 4/2007 |

(Continued)

OTHER PUBLICATIONS

Davenport et al., "The Potential For Artificial Intelligence In Healthcare", 2019, Future Healthcare Journal 2019, vol. 6, No. 2: Year: 2019, pp. 1-5.
(Continued)

*Primary Examiner* — George Manuel
(74) *Attorney, Agent, or Firm* — Dickinson Wright PLLC; Jonathan H. Harder; Stephen A. Mason

(57) ABSTRACT

A computer-implemented system for a remote examination is disclosed. The computer-implemented system includes a treatment device, a master console, a user interface, and a control system. The treatment device comprises one or more slave sensors and a slave pressure system, the treatment device configured to be manipulated while a patient performs a treatment plan. The master console comprises a master device. The user interface comprises an output device configured to present telemedicine information associated with a telemedicine session. The control system comprises one or more processing devices operatively coupled to the master console and the treatment device. The one or more processing devices are configured to receive slave sensor
(Continued)

data from the one or more slave sensors, use a manipulation of the master device to generate a manipulation instruction, transmit the manipulation instruction, and during the telemedicine session, use the manipulation instruction to cause the slave pressure system to activate.

20 Claims, 11 Drawing Sheets

Related U.S. Application Data continuation of application No. 17/147,532, filed on Jan. 13, 2021, which is a continuation-in-part of application No. 17/021,895, filed on Sep. 15, 2020, now Pat. No. 11,071,597.

(60) Provisional application No. 63/018,834, filed on May 1, 2020, provisional application No. 62/910,232, filed on Oct. 3, 2019.

(58) Field of Classification Search
CPC ...... A61B 5/7465; G16H 20/30; G16H 40/67; G16H 50/20; G16H 80/00
See application file for complete search history.

(56) References Cited

U.S. PATENT DOCUMENTS

| | | |
|---|---|---|
| 4,822,032 A | 4/1989 | Whitmore et al. |
| 4,860,763 A | 8/1989 | Schminke |
| 4,869,497 A | 9/1989 | Stewart et al. |
| 4,932,650 A | 6/1990 | Bingham et al. |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,356,356 A | 10/1994 | Hildebrandt |
| 5,361,649 A | 11/1994 | Slocum, Jr. |
| D359,777 S | 6/1995 | Hildebrandt |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,007,459 A | 12/1999 | Burgess |
| D421,075 S | 2/2000 | Hildebrandt |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| 6,640,662 B1 | 11/2003 | Baxter |
| 6,652,425 B1 | 11/2003 | Martin et al. |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| 7,507,188 B2 | 3/2009 | Nurre |
| 7,594,879 B2 | 9/2009 | Johnson |
| 7,628,730 B1 | 12/2009 | Watterson et al. |
| D610,635 S | 2/2010 | Hildebrandt |
| 7,778,851 B2 | 8/2010 | Schoenberg et al. |
| 7,809,601 B2 | 10/2010 | Shaya et al. |
| 7,815,551 B2 | 10/2010 | Merli |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,969,315 B1 | 6/2011 | Ross et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,079,937 B2 | 12/2011 | Bedell et al. |
| 8,113,991 B2 | 2/2012 | Kutliroff |
| 8,177,732 B2 | 5/2012 | Einav et al. |
| 8,287,434 B2 | 10/2012 | Zavadsky et al. |
| 8,298,123 B2 | 10/2012 | Hickman |
| 8,371,990 B2 | 2/2013 | Shea |
| 8,419,593 B2 | 4/2013 | Ainsworth et al. |
| 8,465,398 B2 | 6/2013 | Lee et al. |
| 8,506,458 B2 | 8/2013 | Dugan |
| 8,515,777 B1 | 8/2013 | Rajasenan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,615,529 B2 | 12/2013 | Reiner |
| 8,672,812 B2 | 3/2014 | Dugan |
| 8,751,264 B2 | 6/2014 | Beraja et al. |
| 8,784,273 B2 | 7/2014 | Dugan |
| 8,818,496 B2 | 8/2014 | Dziubinski et al. |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,911,327 B1 | 12/2014 | Boyette |

(56) References Cited

U.S. PATENT DOCUMENTS

| | | |
|---|---|---|
| 8,979,711 B2 | 3/2015 | Dugan |
| 9,004,598 B2 | 4/2015 | Weber |
| 9,044,630 B1 | 6/2015 | Lampert et al. |
| 9,167,281 B2 | 10/2015 | Petrov et al. |
| D744,050 S | 11/2015 | Colburn |
| 9,248,071 B1 | 2/2016 | Benda et al. |
| 9,272,185 B2 | 3/2016 | Dugan |
| 9,283,434 B1 | 3/2016 | Wu |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |
| 9,443,205 B2 | 9/2016 | Wall |
| 9,474,935 B2 | 10/2016 | Abbondanza et al. |
| 9,480,873 B2 | 11/2016 | Chuang |
| 9,481,428 B2 | 11/2016 | Gros et al. |
| 9,514,277 B2 | 12/2016 | Hassing et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,640,057 B1 | 5/2017 | Ross |
| 9,707,147 B2 | 7/2017 | Levital et al. |
| 9,713,744 B2 | 7/2017 | Suzuki |
| D794,142 S | 8/2017 | Zhou |
| 9,717,947 B2 | 8/2017 | Lin |
| 9,737,761 B1 | 8/2017 | Govindarajan |
| 9,757,612 B2 | 9/2017 | Weber |
| 9,782,621 B2 | 10/2017 | Chiang et al. |
| 9,802,076 B2 | 10/2017 | Murray et al. |
| 9,802,081 B2 | 10/2017 | Ridgel et al. |
| 9,813,239 B2 | 11/2017 | Chee et al. |
| 9,827,445 B2 | 11/2017 | Marcos et al. |
| 9,849,337 B2 | 12/2017 | Roman et al. |
| 9,868,028 B2 | 1/2018 | Shin |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 9,977,587 B2 | 5/2018 | Mountain |
| 9,993,181 B2 | 6/2018 | Ross |
| 9,997,082 B2 | 6/2018 | Kaleal |
| 10,004,946 B2 | 6/2018 | Ross |
| 10,026,052 B2 | 7/2018 | Brown et al. |
| D826,349 S | 8/2018 | Oblamski |
| 10,055,550 B2 | 8/2018 | Goetz |
| 10,058,473 B2 | 8/2018 | Oshima et al. |
| 10,074,148 B2 | 9/2018 | Cashman et al. |
| 10,089,443 B2 | 10/2018 | Miller et al. |
| 10,111,643 B2 | 10/2018 | Shulhauser et al. |
| 10,130,311 B1 | 11/2018 | De Sapio et al. |
| 10,137,328 B2 | 11/2018 | Baudhuin |
| 10,143,395 B2 | 12/2018 | Chakravarthy et al. |
| 10,155,134 B2 | 12/2018 | Dugan |
| 10,159,872 B2 | 12/2018 | Sasaki et al. |
| 10,173,094 B2 | 1/2019 | Gomberg et al. |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,258,823 B2 | 4/2019 | Cole |
| 10,325,070 B2 | 6/2019 | Beale et al. |
| 10,327,697 B1 | 6/2019 | Stein et al. |
| 10,369,021 B2 | 8/2019 | Zoss et al. |
| 10,380,866 B1 | 8/2019 | Ross et al. |
| 10,413,222 B1 | 9/2019 | Kayyali |
| 10,413,238 B1 | 9/2019 | Cooper |
| 10,424,033 B2 | 9/2019 | Romeo |
| 10,430,552 B2 | 10/2019 | Mihai |
| D866,957 S | 11/2019 | Ross et al. |
| 10,468,131 B2 | 11/2019 | Macoviak et al. |
| 10,475,323 B1 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,581,896 B2 | 3/2020 | Nachenberg |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| D899,605 S | 10/2020 | Ross et al. |
| 10,792,495 B2 | 10/2020 | Izvorski et al. |
| 10,814,170 B2 | 10/2020 | Wang et al. |
| 10,857,426 B1 | 12/2020 | Neumann |
| 10,867,695 B2 | 12/2020 | Neagle |
| 10,874,905 B2 | 12/2020 | Belson et al. |
| D907,143 S | 1/2021 | Ach et al. |
| 10,881,911 B2 | 1/2021 | Kwon et al. |
| 10,918,332 B2 | 2/2021 | Belson et al. |
| 10,931,643 B1 | 2/2021 | Neumann |
| 10,987,176 B2 | 4/2021 | Poltaretskyi et al. |
| 10,991,463 B2 | 4/2021 | Kutzko et al. |
| 11,000,735 B2 | 5/2021 | Orady et al. |
| 11,045,709 B2 | 6/2021 | Putnam |
| 11,065,170 B2 | 7/2021 | Yang et al. |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,094,400 B2 | 8/2021 | Riley et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| 11,185,738 B1 | 11/2021 | McKirdy et al. |
| D939,096 S | 12/2021 | Lee |
| D939,644 S | 12/2021 | Ach et al. |
| D940,797 S | 1/2022 | Ach et al. |
| D940,891 S | 1/2022 | Lee |
| 11,229,727 B2 | 1/2022 | Tatonetti |
| 11,265,234 B2 | 3/2022 | Guaneri et al. |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,298,284 B2 | 4/2022 | Bayerlein |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,347,829 B1 | 5/2022 | Sclar et al. |
| 11,348,683 B2 | 5/2022 | Guaneri et al. |
| 11,376,470 B2 | 7/2022 | Weldemariam |
| 11,404,150 B2 | 8/2022 | Guaneri et al. |
| 11,410,768 B2 | 8/2022 | Mason et al. |
| 11,422,841 B2 | 8/2022 | Jeong |
| 11,437,137 B1 | 9/2022 | Harris |
| 11,495,355 B2 | 11/2022 | McNutt et al. |
| 11,508,258 B2 | 11/2022 | Nakashima et al. |
| 11,508,482 B2 | 11/2022 | Mason et al. |
| 11,515,021 B2 | 11/2022 | Mason |
| 11,515,028 B2 | 11/2022 | Mason |
| 11,524,210 B2 | 12/2022 | Kim et al. |
| 11,527,326 B2 | 12/2022 | McNair et al. |
| 11,532,402 B2 | 12/2022 | Farley et al. |

(56) References Cited

U.S. PATENT DOCUMENTS

| | | |
|---|---|---|
| 11,534,654 B2 | 12/2022 | Silcock et al. |
| D976,339 S | 1/2023 | Li |
| 11,541,274 B2 | 1/2023 | Hacking |
| 11,621,067 B1 | 4/2023 | Nolan |
| 11,636,944 B2 | 4/2023 | Hanrahan et al. |
| 11,654,327 B2 | 5/2023 | Phillips et al. |
| 11,663,673 B2 | 5/2023 | Pyles |
| 11,701,548 B2 | 7/2023 | Posnack et al. |
| 11,957,960 B2 | 4/2024 | Bissonnette et al. |
| 12,057,210 B2 | 8/2024 | Akinola et al. |
| 2001/0044573 A1 | 11/2001 | Manoli |
| 2002/0010596 A1 | 1/2002 | Matory |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0064860 A1 | 4/2003 | Yamashita et al. |
| 2003/0064863 A1 | 4/2003 | Chen |
| 2003/0083596 A1 | 5/2003 | Kramer et al. |
| 2003/0092536 A1 | 5/2003 | Romanelli et al. |
| 2003/0181832 A1 | 9/2003 | Carnahan et al. |
| 2004/0072652 A1 | 4/2004 | Alessandri et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0197727 A1 | 10/2004 | Sachdeva et al. |
| 2004/0204959 A1 | 10/2004 | Moreano et al. |
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0115561 A1 | 6/2005 | Stahmann |
| 2005/0143641 A1 | 6/2005 | Tashiro |
| 2005/0274220 A1 | 12/2005 | Reboullet |
| 2006/0003871 A1 | 1/2006 | Houghton et al. |
| 2006/0046905 A1 | 3/2006 | Doody, Jr. et al. |
| 2006/0058648 A1 | 3/2006 | Meier |
| 2006/0064136 A1 | 3/2006 | Wang |
| 2006/0064329 A1 | 3/2006 | Abolfathi et al. |
| 2006/0129432 A1 | 6/2006 | Choi et al. |
| 2006/0199700 A1 | 9/2006 | LaStayo et al. |
| 2006/0247095 A1 | 11/2006 | Rummerfield |
| 2007/0042868 A1 | 2/2007 | Fisher et al. |
| 2007/0118389 A1 | 5/2007 | Shipon |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0271065 A1 | 11/2007 | Gupta et al. |
| 2007/0287597 A1 | 12/2007 | Cameron |
| 2008/0021834 A1 | 1/2008 | Holla et al. |
| 2008/0077619 A1 | 3/2008 | Gilley et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0183500 A1 | 7/2008 | Banigan |
| 2008/0281633 A1 | 11/2008 | Burdea et al. |
| 2008/0300914 A1 | 12/2008 | Karkanias et al. |
| 2009/0011907 A1 | 1/2009 | Radow et al. |
| 2009/0058635 A1 | 3/2009 | LaLonde et al. |
| 2009/0070138 A1 | 3/2009 | Langheier et al. |
| 2009/0211395 A1 | 8/2009 | Mule |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0248905 A1 | 9/2010 | Lu |
| 2010/0262052 A1 | 10/2010 | Lunau et al. |
| 2010/0268304 A1 | 10/2010 | Matos |
| 2010/0298102 A1 | 11/2010 | Bosecker et al. |
| 2010/0326207 A1 | 12/2010 | Topel |
| 2011/0010188 A1 | 1/2011 | Yoshikawa et al. |
| 2011/0047108 A1 | 2/2011 | Chakrabarty et al. |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0275483 A1 | 11/2011 | Dugan |
| 2011/0281249 A1 | 11/2011 | Gammell et al. |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0130196 A1 | 5/2012 | Jain et al. |
| 2012/0130197 A1 | 5/2012 | Kugler et al. |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0259648 A1 | 10/2012 | Mallon et al. |
| 2012/0259649 A1 | 10/2012 | Mallon et al. |
| 2012/0278759 A1 | 11/2012 | Curl et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0108594 A1 | 5/2013 | Martin-Rendon et al. |
| 2013/0110545 A1 | 5/2013 | Smallwood |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0137552 A1 | 5/2013 | Kemp et al. |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0031174 A1 | 1/2014 | Huang |
| 2014/0062900 A1 | 3/2014 | Kaula et al. |
| 2014/0074179 A1 | 3/2014 | Heldman et al. |
| 2014/0089836 A1 | 3/2014 | Damani et al. |
| 2014/0113261 A1 | 4/2014 | Akiba |
| 2014/0113768 A1 | 4/2014 | Lin et al. |
| 2014/0155129 A1 | 6/2014 | Dugan |
| 2014/0163439 A1 | 6/2014 | Uryash et al. |
| 2014/0172442 A1 | 6/2014 | Broderick |
| 2014/0172460 A1 | 6/2014 | Kohli |
| 2014/0172514 A1 | 6/2014 | Schumann et al. |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0303540 A1 | 10/2014 | Baym |
| 2014/0309083 A1 | 10/2014 | Dugan |
| 2014/0322686 A1 | 10/2014 | Kang |
| 2014/0347265 A1 | 11/2014 | Aimone et al. |
| 2014/0371816 A1 | 12/2014 | Matos |
| 2014/0372133 A1 | 12/2014 | Austrum et al. |

(56) References Cited

U.S. PATENT DOCUMENTS

| | | |
|---|---|---|
| 2015/0025816 A1 | 1/2015 | Ross |
| 2015/0045700 A1 | 2/2015 | Cavanagh et al. |
| 2015/0051721 A1 | 2/2015 | Cheng |
| 2015/0065213 A1 | 3/2015 | Dugan |
| 2015/0073814 A1 | 3/2015 | Linebaugh |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0111644 A1 | 4/2015 | Larson |
| 2015/0112230 A1 | 4/2015 | Iglesias |
| 2015/0112702 A1 | 4/2015 | Joao et al. |
| 2015/0130830 A1 | 5/2015 | Nagasaki |
| 2015/0141200 A1 | 5/2015 | Murray et al. |
| 2015/0142142 A1 | 5/2015 | Aguilera et al. |
| 2015/0149217 A1 | 5/2015 | Kaburagi |
| 2015/0151162 A1 | 6/2015 | Dugan |
| 2015/0161331 A1 | 6/2015 | Oleynik |
| 2015/0161876 A1 | 6/2015 | Castillo |
| 2015/0174446 A1 | 6/2015 | Chiang |
| 2015/0196805 A1 | 7/2015 | Koduri |
| 2015/0217056 A1 | 8/2015 | Kadavy et al. |
| 2015/0251074 A1 | 9/2015 | Ahmed et al. |
| 2015/0257679 A1 | 9/2015 | Ross |
| 2015/0265209 A1 | 9/2015 | Zhang |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0004820 A1 | 1/2016 | Moore |
| 2016/0007885 A1 | 1/2016 | Basta et al. |
| 2016/0015995 A1 | 1/2016 | Leung et al. |
| 2016/0023081 A1 | 1/2016 | Popa-Simil et al. |
| 2016/0045170 A1 | 2/2016 | Migita |
| 2016/0096073 A1 | 4/2016 | Rahman et al. |
| 2016/0117471 A1 | 4/2016 | Belt et al. |
| 2016/0132643 A1 | 5/2016 | Radhakrishna et al. |
| 2016/0140319 A1 | 5/2016 | Stark |
| 2016/0143593 A1 | 5/2016 | Fu et al. |
| 2016/0151670 A1 | 6/2016 | Dugan |
| 2016/0158534 A1 | 6/2016 | Guarraia et al. |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0197918 A1 | 7/2016 | Turgeman et al. |
| 2016/0213924 A1 | 7/2016 | Coleman |
| 2016/0275259 A1 | 9/2016 | Nolan et al. |
| 2016/0287166 A1 | 10/2016 | Tran |
| 2016/0302666 A1 | 10/2016 | Shaya |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0345841 A1 | 12/2016 | Jang et al. |
| 2016/0354636 A1 | 12/2016 | Jang |
| 2016/0361597 A1 | 12/2016 | Cole et al. |
| 2016/0373477 A1 | 12/2016 | Moyle |
| 2017/0004260 A1 | 1/2017 | Moturu et al. |
| 2017/0011179 A1 | 1/2017 | Arshad et al. |
| 2017/0032092 A1 | 2/2017 | Mink et al. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0091422 A1 | 3/2017 | Kumar et al. |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0202724 A1 | 7/2017 | De Rossi |
| 2017/0209766 A1 | 7/2017 | Riley et al. |
| 2017/0220751 A1 | 8/2017 | Davis |
| 2017/0228517 A1 | 8/2017 | Saliman et al. |
| 2017/0235882 A1 | 8/2017 | Orlov et al. |
| 2017/0235906 A1 | 8/2017 | Dorris et al. |
| 2017/0243028 A1 | 8/2017 | LaFever et al. |
| 2017/0262604 A1 | 9/2017 | Francois |
| 2017/0265800 A1 | 9/2017 | Auchinleck et al. |
| 2017/0266501 A1 | 9/2017 | Sanders et al. |
| 2017/0270260 A1 | 9/2017 | Shetty |
| 2017/0278209 A1 | 9/2017 | Olsen et al. |
| 2017/0282015 A1 | 10/2017 | Wicks et al. |
| 2017/0283508 A1 | 10/2017 | Demopulos et al. |
| 2017/0286621 A1 | 10/2017 | Cox |
| 2017/0296861 A1 | 10/2017 | Burkinshaw |
| 2017/0300654 A1 | 10/2017 | Stein et al. |
| 2017/0304024 A1 | 10/2017 | Nobrega |
| 2017/0312614 A1 | 11/2017 | Tran et al. |
| 2017/0323481 A1 | 11/2017 | Tran et al. |
| 2017/0329917 A1 | 11/2017 | McRaith et al. |
| 2017/0329933 A1 | 11/2017 | Brust |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0347923 A1 | 12/2017 | Roh |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0036591 A1 | 2/2018 | King et al. |
| 2018/0036593 A1 | 2/2018 | Ridgel et al. |
| 2018/0052962 A1 | 2/2018 | Van Der Koijk et al. |
| 2018/0056104 A1 | 3/2018 | Cromie et al. |
| 2018/0060494 A1 | 3/2018 | Dias et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0096111 A1 | 4/2018 | Wells et al. |
| 2018/0099178 A1 | 4/2018 | Schaefer et al. |
| 2018/0102190 A1 | 4/2018 | Hogue et al. |
| 2018/0113985 A1 | 4/2018 | Gandy et al. |
| 2018/0116741 A1 | 5/2018 | Garcia Kilroy et al. |
| 2018/0117417 A1 | 5/2018 | Davis |
| 2018/0130555 A1 | 5/2018 | Chronis et al. |
| 2018/0140927 A1 | 5/2018 | Kito |
| 2018/0146870 A1 | 5/2018 | Shemesh |
| 2018/0177612 A1 | 6/2018 | Trabish et al. |
| 2018/0178061 A1 | 6/2018 | O'Larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0236307 A1 | 8/2018 | Hyde et al. |
| 2018/0240552 A1 | 8/2018 | Tuyl et al. |
| 2018/0253991 A1 | 9/2018 | Tang et al. |
| 2018/0255110 A1 | 9/2018 | Dowlatkhah et al. |
| 2018/0256079 A1 | 9/2018 | Yang et al. |
| 2018/0263530 A1 | 9/2018 | Jung |
| 2018/0263535 A1 | 9/2018 | Cramer |
| 2018/0263552 A1 | 9/2018 | Graman et al. |

(56) References Cited

U.S. PATENT DOCUMENTS

| | | |
|---|---|---|
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296143 A1 | 10/2018 | Anderson et al. |
| 2018/0296157 A1 | 10/2018 | Bleich et al. |
| 2018/0318122 A1 | 11/2018 | LeCursi et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0290017 A1 | 12/2018 | Fung |
| 2018/0353812 A1 | 12/2018 | Lannon et al. |
| 2018/0360340 A1 | 12/2018 | Rehse et al. |
| 2018/0366225 A1 | 12/2018 | Mansi et al. |
| 2018/0373844 A1 | 12/2018 | Ferrandez-Escamez et al. |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0083846 A1 | 3/2019 | Eder |
| 2019/0088356 A1 | 3/2019 | Oliver et al. |
| 2019/0090744 A1 | 3/2019 | Mahfouz |
| 2019/0096534 A1 | 3/2019 | Joao |
| 2019/0105551 A1 | 4/2019 | Ray |
| 2019/0111299 A1 | 4/2019 | Radcliffe et al. |
| 2019/0115097 A1 | 4/2019 | Macoviak et al. |
| 2019/0117156 A1 | 4/2019 | Howard et al. |
| 2019/0118038 A1 | 4/2019 | Tana et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0143191 A1 | 5/2019 | Ran et al. |
| 2019/0145774 A1 | 5/2019 | Ellis |
| 2019/0163876 A1 | 5/2019 | Remme et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0214119 A1 | 7/2019 | Wachira et al. |
| 2019/0223797 A1 | 7/2019 | Tran |
| 2019/0224528 A1 | 7/2019 | Omid-Zohoor et al. |
| 2019/0228856 A1 | 7/2019 | Leifer |
| 2019/0232108 A1 | 8/2019 | Kovach et al. |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0251456 A1 | 8/2019 | Constantin |
| 2019/0261959 A1* | 8/2019 | Frankel ................ A61B 8/4218 |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0385199 A1 | 12/2019 | Bender et al. |
| 2019/0388728 A1 | 12/2019 | Wang et al. |
| 2019/0392936 A1 | 12/2019 | Arric et al. |
| 2019/0392939 A1 | 12/2019 | Basta et al. |
| 2020/0005928 A1 | 1/2020 | Daniel |
| 2020/0034707 A1 | 1/2020 | Kivatinos et al. |
| 2020/0038703 A1 | 2/2020 | Cleary et al. |
| 2020/0051446 A1 | 2/2020 | Rubinstein et al. |
| 2020/0066390 A1 | 2/2020 | Svendrys et al. |
| 2020/0085300 A1 | 3/2020 | Kwatra et al. |
| 2020/0090802 A1 | 3/2020 | Maron |
| 2020/0093418 A1 | 3/2020 | Kluger et al. |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0237291 A1 | 7/2020 | Raja |
| 2020/0237452 A1 | 7/2020 | Wolf et al. |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0312447 A1 | 10/2020 | Bohn et al. |
| 2020/0334972 A1 | 10/2020 | Gopalakrishnan |
| 2020/0353314 A1 | 11/2020 | Messinger |
| 2020/0357299 A1 | 11/2020 | Patel et al. |
| 2020/0365256 A1 | 11/2020 | Hayashitani et al. |
| 2020/0395112 A1 | 12/2020 | Ronner |
| 2020/0401224 A1 | 12/2020 | Cotton |
| 2020/0402662 A1 | 12/2020 | Esmailian et al. |
| 2020/0410374 A1 | 12/2020 | White |
| 2020/0410385 A1 | 12/2020 | Otsuki |
| 2020/0411162 A1 | 12/2020 | Lien et al. |
| 2021/0005224 A1 | 1/2021 | Rothschild et al. |
| 2021/0005319 A1 | 1/2021 | Otsuki et al. |
| 2021/0008413 A1 | 1/2021 | Asikainen et al. |
| 2021/0027889 A1 | 1/2021 | Neil et al. |
| 2021/0035674 A1 | 2/2021 | Volosin et al. |
| 2021/0050086 A1 | 2/2021 | Rose et al. |
| 2021/0065855 A1 | 3/2021 | Pepin et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0187348 A1 | 6/2021 | Phillips et al. |
| 2021/0202090 A1 | 7/2021 | ODonovan et al. |
| 2021/0202103 A1 | 7/2021 | Bostic et al. |
| 2021/0236020 A1 | 8/2021 | Matijevich et al. |
| 2021/0244998 A1 | 8/2021 | Hacking et al. |
| 2021/0245003 A1 | 8/2021 | Turner |

(56) References Cited

U.S. PATENT DOCUMENTS

| | | |
|---|---|---|
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0361514 A1 | 11/2021 | Choi et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack et al. |
| 2022/0016480 A1 | 1/2022 | Bissonnette et al. |
| 2022/0016482 A1 | 1/2022 | Bissonnette |
| 2022/0016485 A1 | 1/2022 | Bissonnette et al. |
| 2022/0016486 A1 | 1/2022 | Bissonnette |
| 2022/0020469 A1 | 1/2022 | Tanner |
| 2022/0044806 A1 | 2/2022 | Sanders et al. |
| 2022/0047921 A1 | 2/2022 | Bissonnette et al. |
| 2022/0079690 A1 | 3/2022 | Mason et al. |
| 2022/0080256 A1 | 3/2022 | Am et al. |
| 2022/0080265 A1 | 3/2022 | Watterson |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0118218 A1 | 4/2022 | Bense et al. |
| 2022/0122724 A1 | 4/2022 | Durlach et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0176039 A1 | 6/2022 | Lintereur et al. |
| 2022/0181004 A1 | 6/2022 | Zilca et al. |
| 2022/0193491 A1 | 6/2022 | Mason et al. |
| 2022/0230729 A1 | 7/2022 | Mason |
| 2022/0238222 A1 | 7/2022 | Neuberg |
| 2022/0238223 A1 | 7/2022 | Mason et al. |
| 2022/0258935 A1 | 8/2022 | Kraft |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305328 A1 | 9/2022 | Choi et al. |
| 2022/0314072 A1 | 10/2022 | Bissonnette et al. |
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0370851 A1 | 11/2022 | Guidarelli et al. |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0029639 A1 | 2/2023 | Roy |
| 2023/0047253 A1 | 2/2023 | Gnanasambandam et al. |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377710 A1 | 11/2023 | Chen et al. |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0395231 A1 | 12/2023 | Rosenberg |
| 2023/0395232 A1 | 12/2023 | Rosenberg |
| 2024/0029856 A1 | 1/2024 | Rosenberg |

FOREIGN PATENT DOCUMENTS

| | | |
|---|---|---|
| CN | 101964151 A | 2/2011 |
| CN | 201889024 U | 7/2011 |
| CN | 202220794 U | 5/2012 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 105620643 A | 6/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107066819 A | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 108078737 A | 5/2018 |
| CN | 208224811 A | 12/2018 |
| CN | 109191954 A | 1/2019 |
| CN | 109363887 A | 2/2019 |
| CN | 208573971 U | 3/2019 |
| CN | 110148472 A | 8/2019 |
| CN | 110201358 A | 9/2019 |

(56) References Cited

FOREIGN PATENT DOCUMENTS

| | | |
|---|---|---|
| CN | 110215188 A | 9/2019 |
| CN | 110322957 A | 10/2019 |
| CN | 110808092 A | 2/2020 |
| CN | 110931103 A | 3/2020 |
| CN | 110993057 A | 4/2020 |
| CN | 111105859 A | 5/2020 |
| CN | 111111110 A | 5/2020 |
| CN | 111370088 A | 7/2020 |
| CN | 111460305 A | 7/2020 |
| CN | 111790111 A | 10/2020 |
| CN | 112071393 A | 12/2020 |
| CN | 212141371 U | 12/2020 |
| CN | 112289425 A | 1/2021 |
| CN | 212624809 U | 2/2021 |
| CN | 112603295 A | 4/2021 |
| CN | 213190965 U | 5/2021 |
| CN | 113384850 A | 9/2021 |
| CN | 113499572 A | 10/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 114632302 A | 6/2022 |
| CN | 114694824 A | 7/2022 |
| CN | 114898832 A | 8/2022 |
| CN | 114983760 A | 9/2022 |
| CN | 217472652 U | 9/2022 |
| CN | 110270062 B | 10/2022 |
| CN | 218420859 U | 2/2023 |
| CN | 115954081 A | 4/2023 |
| DE | 95019 C | 1/1897 |
| DE | 7628633 U1 | 12/1977 |
| DE | 8519150 U1 | 10/1985 |
| DE | 3732905 A1 | 7/1988 |
| DE | 19619820 A1 | 12/1996 |
| DE | 29620008 U1 | 2/1997 |
| DE | 19947926 A1 | 4/2001 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 0383137 A2 | 8/1990 |
| EP | 634319 A2 | 1/1995 |
| EP | 0919259 A1 | 6/1999 |
| EP | 1034817 A1 | 9/2000 |
| EP | 1159989 A1 | 12/2001 |
| EP | 1391179 A1 | 2/2004 |
| EP | 1968028 | 9/2008 |
| EP | 2564904 A1 | 3/2013 |
| EP | 2575064 A1 | 4/2013 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3264303 A1 | 1/2018 |
| EP | 3323473 A1 | 5/2018 |
| EP | 3547322 A1 | 10/2019 |
| EP | 3627514 A1 | 3/2020 |
| EP | 3671700 A1 | 6/2020 |
| EP | 3688537 A1 | 8/2020 |
| EP | 3731733 A1 | 11/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |
| EP | 4112033 A1 | 1/2023 |
| FR | 2527541 A2 | 12/1983 |
| FR | 3127393 A1 | 3/2023 |
| GB | 141664 A | 11/1920 |
| GB | 2336140 A | 10/1999 |
| GB | 2372459 A | 8/2002 |
| GB | 2512431 A | 10/2014 |
| GB | 2591542 B | 3/2022 |
| IN | 201811043670 A | 7/2018 |
| JP | 2000005339 A | 1/2000 |
| JP | 2003225875 A | 8/2003 |
| JP | 2005227928 A | 8/2005 |
| JP | 2005227928 A1 | 8/2005 |
| JP | 2009112336 A | 5/2009 |
| JP | 2013515995 A | 5/2013 |
| JP | 2014104139 A | 6/2014 |
| JP | 3193662 U | 10/2014 |
| JP | 3198173 U | 6/2015 |
| JP | 5804063 B2 | 11/2015 |
| JP | 2018102842 A | 7/2018 |
| JP | 2019028647 A | 2/2019 |
| JP | 2019134909 A | 8/2019 |
| JP | 6573739 B1 | 9/2019 |
| JP | 6659831 B2 | 3/2020 |
| JP | 2020057082 A | 4/2020 |
| JP | 6710357 B1 | 6/2020 |
| JP | 6775757 B1 | 10/2020 |
| JP | 2021027917 A | 2/2021 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 20020009724 A | 2/2002 |
| KR | 200276919 Y1 | 5/2002 |
| KR | 20020065253 A | 8/2002 |
| KR | 100582596 B1 | 5/2006 |
| KR | 101042258 B1 | 6/2011 |
| KR | 101258250 B1 | 4/2013 |
| KR | 101325581 B1 | 11/2013 |
| KR | 20140128630 A | 11/2014 |
| KR | 20150017693 A | 2/2015 |
| KR | 20150078191 A | 7/2015 |
| KR | 101580071 B1 | 12/2015 |
| KR | 101647620 B1 | 8/2016 |
| KR | 20160093990 A | 8/2016 |
| KR | 20170038837 A | 4/2017 |
| KR | 20180004928 A | 1/2018 |
| KR | 20190029175 A | 3/2019 |
| KR | 20190056116 A | 5/2019 |
| KR | 101988167 B1 | 6/2019 |
| KR | 101969392 B1 | 8/2019 |
| KR | 102055279 B1 | 12/2019 |
| KR | 102088333 B1 | 3/2020 |
| KR | 20200025290 A | 3/2020 |
| KR | 20200029180 A | 3/2020 |
| KR | 102097190 B1 | 4/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102121586 B1 | 6/2020 |
| KR | 102142713 B1 | 8/2020 |
| KR | 102162522 B1 | 10/2020 |
| KR | 20200119665 A | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102264498 B1 | 6/2021 |
| KR | 102352602 B1 | 1/2022 |
| KR | 102352603 B1 | 1/2022 |
| KR | 102352604 B1 | 1/2022 |

(56) References Cited

FOREIGN PATENT DOCUMENTS

| | | |
|---|---|---|
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| NO | 2022212921 A1 | 10/2022 |
| RU | 2014131288 A | 2/2016 |
| RU | 2607953 C2 | 1/2017 |
| TW | M474545 U | 3/2014 |
| TW | I442956 B | 7/2014 |
| TW | M638437 U | 3/2023 |
| WO | 1998009687 A1 | 3/1998 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02062211 A2 | 8/2002 |
| WO | 02093312 A2 | 11/2002 |
| WO | 2003043494 A1 | 5/2003 |
| WO | 2005018453 A1 | 3/2005 |
| WO | 2006004430 A2 | 1/2006 |
| WO | 2006012694 A1 | 2/2006 |
| WO | 2007102709 A1 | 9/2007 |
| WO | 2008114291 A1 | 9/2008 |
| WO | 2009003170 A1 | 12/2008 |
| WO | 2009008968 A1 | 1/2009 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016151364 A1 | 9/2016 |
| WO | 2016154318 A1 | 9/2016 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2018081795 A1 | 5/2018 |
| WO | 2018171853 A1 | 9/2018 |
| WO | 2019022706 A1 | 1/2019 |
| WO | 2019143940 A1 | 7/2019 |
| WO | 2020075190 A1 | 4/2020 |
| WO | 2020130979 A1 | 6/2020 |
| WO | 2020149815 A2 | 7/2020 |
| WO | 2020229705 A1 | 11/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021022003 A1 | 2/2021 |
| WO | 2021038980 A1 | 3/2021 |
| WO | 2021055427 A1 | 3/2021 |
| WO | 2021061061 A1 | 4/2021 |
| WO | 2021090267 A1 | 5/2021 |
| WO | 2021138620 A1 | 7/2021 |
| WO | 2021236961 A1 | 11/2021 |
| WO | 2022047006 A1 | 3/2022 |
| WO | 2022092493 A1 | 5/2022 |
| WO | 2022092494 A1 | 5/2022 |
| WO | 2022212883 A1 | 10/2022 |
| WO | 2022216498 A1 | 10/2022 |
| WO | 2022251420 A1 | 12/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |
| WO | 2023052695 A1 | 4/2023 |
| WO | 2023091496 A1 | 5/2023 |
| WO | 2023215155 A1 | 11/2023 |
| WO | 2023230075 A1 | 11/2023 |
| WO | 2024013267 A1 | 1/2024 |
| WO | 2024107807 A1 | 5/2024 |

OTHER PUBLICATIONS

Ahmed et al., "Artificial Intelligence With Multi-Functional Machine Learning Platform Development For Better Healthcare And Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pages 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Gerbild et al., "Physical Activity to Improve Erectile Dysfunction: A Systematic Review of Intervention Studies," Sexual Medicine, 2018, 15 pages.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the PAR-Q+ And ePARmed-X+ Validation of the PAR-Q+ and ePARmed-X+," Health & Fitness Journal of Canada, 2011, 9 pages, vol. 4, No. 2.

Jeong et al., "Computer-assisted upper extremity training using interactive biking exercise (iBikE) platform," Sep. 2012, pp. 1-5, 34th Annual International Conference of the IEEE EMBS.

HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.

International Preliminary Report on Patentability of International Application No. PCT/US2017/50895, Date of Mailing Dec. 11, 2018, 52 pages.

International Searching Authority, Search Report and Written Opinion for International Application No. PCT/US2017/50895, Date of Mailing Jan. 12, 2018, 6 pages.

(56) References Cited

OTHER PUBLICATIONS

International Searching Authority, Search Report and Written Opinion for International Application No. PCT/US2020/021876, Date of Mailing May 28, 2020, 8 pages.
International Searching Authority, Search Report and Written Opinion for International Application No. PCT/US2020/051008, Date of Mailing Dec. 10, 2020, 9 pages.
International Searching Authority, Search Report and Written Opinion for International Application No. PCT/US2020/056661, Date of Mailing Feb. 12, 2021, 12 pages.
International Searching Authority, Search Report and Written Opinion for International Application No. PCT/US2021/032807, Date of Mailing Sep. 6, 2021, 11 pages.
Matrix, R3xm Recumbent Cycle, retrieved on Aug. 4, 2020, 7 pages, https://www.matrixfitness.com/en/cardio/cycles/r3xm-recumbent.
ROM3 Rehab, ROM3 Rehab System, Apr. 20, 2015, retrieved on Aug. 31, 2018, 12 pages, https://vimeo.com/125438463.
Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.
International Search Report and Written Opinion for PCT/US2023/014137, dated Jun. 9, 2023, 13 pages.
Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZlwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform For Personalized Predictive Analytics", ProQuest LLC, Jul. 2017, 185 pages.
Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.
Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.
Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.
Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.
Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health Networking, Applications and Services, Columbia, MO, USA, 2011, 6 pages.
Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.
Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.
Zakari et al., "Are There Limitations to Exercise Benefits in Peripheral Arterial Disease?," Frontiers in Cardiovascular Medicine, Nov. 2018, vol. 5, Article 173, 12 pages.
You et al., "Including Blood Vasculature into a Game-Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE EMBS, 5 pages.
Website for "Pedal Exerciser", p. 1, retrieved on Sep. 9, 2022 from https://www.vivehealth.com/collections/physical-therapy-equipment/products/pedalexerciser.
Website for "Functional Knee Brace with ROM", p. 1, retrieved on Sep. 9, 2022 from http://medicalbrace.gr/en/product/functional-knee-brace-with-goniometer-mbtelescopicknee/.
Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-US/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
Barrett et al., "Artificial intelligence supported patient self-care in chronic heart failure: a paradigm shift from reactive to predictive, preventive and personalised care," EPMA Journal (2019), pp. 445-464.
Oerkild et al., "Home-based cardiac rehabilitation is an attractive alternative to No. cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.
Thomas et al., "Home-Based Cardiac Rehabilitation," Circulation, 2019, pp. e69-e89, vol. 140.

(56) References Cited

OTHER PUBLICATIONS

Thomas et al., "Home-Based Cardiac Rehabilitation," Journal of the American College of Cardiology, Nov. 1, 2019, pp. 133-153, vol. 74.
Thomas et al., "Home-Based Cardiac Rehabilitation," HHS Public Access, Oct. 2, 2020, pp. 1-39.
Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.
Chen et al., "Home-based cardiac rehabilitation improves quality of life, aerobic capacity, and readmission rates in patients with chronic heart failure," Medicine, 2018, pp. 1-5 Vol. 97:4.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.
Beene et al., "AI and Care Delivery: Emerging Opportunities For Artificial Intelligence To Transform How Care Is Delivered," Nov. 2019, American Hospital Association, pp. 1-12.
Jeong et al., "Remotely controlled biking is associated with improved adherence to prescribed cycling speed," Technology and Health Care 23, 2015, 7 pages.
Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.
Blasiak et al., "Curate.AI: Optimizing Personalized Medicine with Artificial Intelligence,"SLAS Technology: Translating Life Sciences Innovation, 2020, 11 pages.
Ahmed et al., "Artificial Intelligence With Multi-Functional Machine Learning Platform Development For Better Healthcare And Precision Medicine," Database (Oxford), 2020, pp. 1-35, vol. 2020.
Davenport et al., "The Potential For Artificial Intelligence in Healthcare," Future Healthcare Journal, 2019, pp. 94-98, vol. 6, No. 2.

* cited by examiner

REMOTE EXAMINATION THROUGH AUGMENTED REALITY

CROSS-REFERENCES TO RELATED APPLICATIONS

This application is a continuation of U.S. patent application Ser. No. 17/379,533, filed Jul. 19, 2021, titled "Remote Examination Through Augmented Reality", which is a continuation of U.S. patent application Ser. No. 17/147,532, filed Jan. 13, 2021, titled "Remote Examination Through Augmented Reality", which is a continuation-in-part of U.S. patent application Ser. No. 17/021,895, filed Sep. 15, 2020, titled "Telemedicine for Orthopedic Treatment", which claims priority to and the benefit of U.S. Provisional Patent Application Ser. No. 62/910,232, filed Oct. 3, 2019, titled "Telemedicine for Orthopedic Treatment", the entire disclosures of which are hereby incorporated by reference for all purposes. U.S. patent application Ser. No. 17/147,532 also claims priority to and the benefit of U.S. Provisional Patent Application Ser. No. 63/018,834, filed May 1, 2020, titled "Remote Examination Through Augmented Reality," the entire disclosure of which are hereby incorporated by reference for all purposes.

TECHNICAL FIELD

This disclosure relates generally to a system and a method for remote examination through augmented reality.

BACKGROUND

Remote medical assistance, also referred to, inter alia, as remote medicine, telemedicine, telemed, telmed, tel-med, or telehealth, is an at least two-way communication between a healthcare provider or providers, such as a physician or a physical therapist, and a patient using audio and/or audio-visual and/or other sensorial or perceptive (e.g., tactile, gustatory, haptic, pressure-sensing-based or electromagnetic (e.g., neurostimulation) communications (e.g., via a computer, a smartphone, or a tablet). Telemedicine may aid a patient in performing various aspects of a rehabilitation regimen for a body part. The patient may use a patient interface in communication with an assistant interface for receiving the remote medical assistance via audio, visual, audiovisual, or other communications described elsewhere herein. Any reference herein to any particular sensorial modality shall be understood to include and to disclose by implication a different one or more sensory modalities.

Telemedicine is an option for healthcare providers to communicate with patients and provide patient care when the patients do not want to or cannot easily go to the healthcare providers' offices. Telemedicine, however, has substantive limitations as the healthcare providers cannot conduct physical examinations of the patients. Rather, the healthcare providers must rely on verbal communication and/or limited remote observation of the patients.

SUMMARY

In general, the present disclosure provides a system and method for remote examination of patients through augmentation.

An aspect of the disclosed embodiments includes a computer-implemented system for a remote examination. The computer-implemented system includes a treatment device, a master console, a user interface, and a control system. The treatment device comprises one or more slave sensors and a slave pressure system, the treatment device configured to be manipulated while a patient performs a treatment plan. The master console comprises a master device. The user interface comprises an output device configured to present telemedicine information associated with a telemedicine session. The control system comprises one or more processing devices operatively coupled to the master console and the treatment device. The one or more processing devices are configured to receive slave sensor data from the one or more slave sensors, use a manipulation of the master device to generate a manipulation instruction, transmit the manipulation instruction, and during the telemedicine session, use the manipulation instruction to cause the slave pressure system to activate.

Another aspect of the disclosed embodiments includes a system for remote examination. The system includes a master console comprising a master device, a treatment device comprising one or more slave sensors and a slave pressure system, and a control system comprising one or more processing devices operatively coupled to the master console and the treatment device. The one or more processing devices are configured to receive slave sensor data from the one or more slave sensors, to use a manipulation of the master device to generate a manipulation instruction, to transmit the manipulation instruction, and to use the manipulation instruction to cause the slave pressure system to activate.

Another aspect of the disclosed embodiments includes a system for remote examination. The system includes a master console comprising a master device, a treatment device comprising one or more slave sensors and a slave pressure system, and a control system comprising one or more processing devices operatively coupled to the master console and the treatment device. The one or more processing devices are configured to receive slave sensor data from the one or more slave sensors, to transmit the slave sensor data, to receive a manipulation instruction, and to use the manipulation instruction to activate the slave pressure system.

Another aspect of the disclosed embodiments includes a system for remote examination. The system includes a master console comprising a master device, a treatment device comprising one or more slave sensors and a slave pressure system, and a control system comprising a master processing device and a slave processing device. The master processing device is operatively coupled to the master console and configured to receive slave sensor data from the slave processing device, to use a manipulation of the master device to generate a manipulation instruction, and to transmit the manipulation instruction to the slave processing device. The slave processing device is operatively coupled to the treatment device and configured to receive the slave sensor data from the one or more slave sensors, to transmit the slave sensor data to the master processing device, to receive the manipulation instruction from the master processing device, and to use the manipulation instruction to activate the slave pressure system.

Another aspect of the disclosed embodiments includes a system that includes a processing device and a memory communicatively coupled to the processing device and capable of storing instructions. The processing device executes the instructions to perform any of the methods, operations, or steps described herein.

Another aspect of the disclosed embodiments includes a tangible, non-transitory computer-readable medium storing instructions that, when executed, cause a processing device to perform any of the methods, operations, or steps described herein.

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

NOTATION AND NOMENCLATURE

Figure 1:
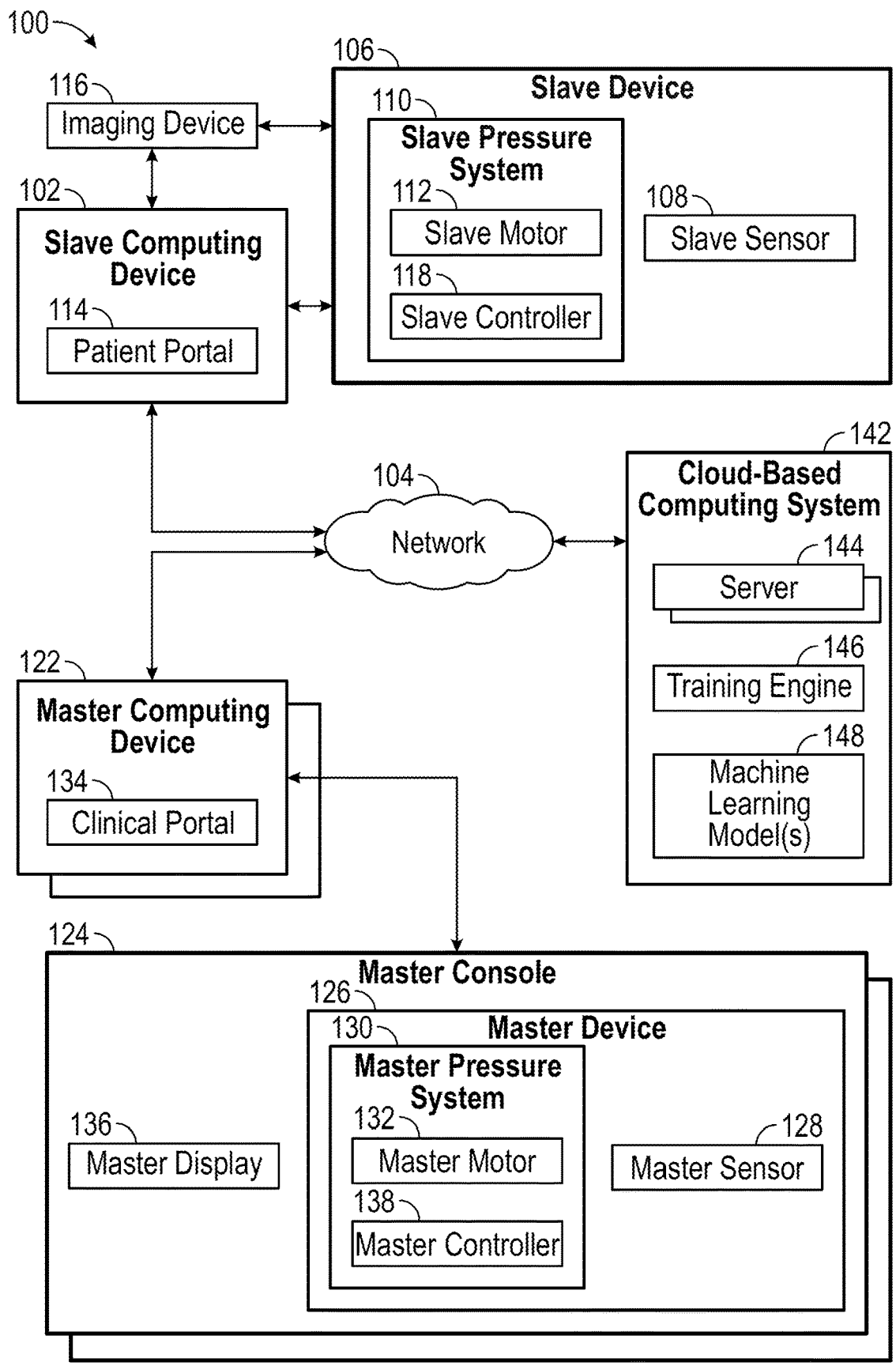
FIG. 1 generally illustrates a high-level component diagram of an illustrative system according to certain aspects of this disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to... ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

The terms telemedicine, telehealth, telemed, teletherapeutic, telemedicine, remote medicine, etc. may be used interchangeably herein.

As used herein, the term healthcare provider may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare provider" may be a human being, a robot, a virtual assistant, a virtual assistant in virtual and/or augmented reality, or an artificially intelligent entity, such entity including a software program, integrated software and hardware, or hardware alone.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining optimal remote examination procedures to create an optimal treatment plan for a patient having certain characteristics (e.g., vital-sign or other measurements; performance; demographic; psychographic; geographic; diagnostic; measurement- or test-based; medically historic; behavioral historic; cognitive; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment device, an amount of force exerted on a portion of the treatment device, a range of motion achieved on the treatment device, a movement speed of a portion of the treatment device, a duration of use of the treatment device, an indication of a plurality of pain levels using the treatment device, or some combination thereof. The measurement information may include, e.g., a vital sign, a respiration rate, a heartrate, a temperature, a blood pressure, a glucose level or other biomarker, or some combination thereof. It may be desirable to process and analyze the characteristics of a multitude of patients, the treatment plans performed for those patients, and the results of the treatment plans for those patients.

Further, another technical problem may involve distally treating, via a computing device during a telemedicine session, a patient from a location different than a location at which the patient is located. An additional technical problem is controlling or enabling, from the different location, the control of a treatment apparatus used by the patient at the patient's location. Oftentimes, when a patient undergoes rehabilitative surgery (e.g., knee surgery), a medical professional may prescribe a treatment apparatus to the patient to use to perform a treatment protocol at their residence or at any mobile location or temporary domicile. A medical professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

When the healthcare provider is located in a location different from the patient and the treatment device, it may be technically challenging for the healthcare provider to monitor the patient's actual progress (as opposed to relying on the patient's word about their progress) in using the treatment device, modify the treatment plan according to the patient's progress, adapt the treatment device to the personal characteristics of the patient as the patient performs the treatment plan, and the like.

Further, in addition to the information described above, determining optimal examination procedures for a particular ailment (e.g., injury, disease, any applicable medical condition, etc.) may include physically examining the injured body part of a patient. The healthcare provider, such as a physician or a physical therapist, may visually inspect the injured body part (e.g., a knee joint). The inspection may include looking for signs of inflammation or injury (e.g., swelling, redness, and warmth), deformity (e.g., symmetrical joints and abnormal contours and/or appearance), or any other suitable observation. To determine limitations of the injured body part, the healthcare provider may observe the injured body part as the patient attempts to perform normal activity (e.g., bending and extending the knee and gauging any limitations to the range of motion of the injured knee). The healthcare provide may use one or more hands and/or fingers to touch the injured body part. By applying pressure to the injured body part, the healthcare provider can obtain information pertaining to the extent of the injury. For example, the healthcare provider's fingers may palpate the injured body part to determine if there is point tenderness, warmth, weakness, strength, or to make any other suitable observation.

It may be desirable to compare characteristics of the injured body part with characteristics of a corresponding non-injured body part to determine what an optimal treatment plan for the patient may be such that the patient can obtain a desired result. Thus, the healthcare provider may examine a corresponding non-injured body part of the patient. For example, the healthcare provider's fingers may palpate a non-injured body part (e.g., a left knee) to determine a baseline of how the patient's non-injured body part feels and functions. The healthcare provider may use the results of the examination of the non-injured body part to determine the extent of the injury to the corresponding injured body part (e.g., a right knee). Additionally, injured body parts may affect other body parts (e.g., a knee injury may limit the use of the affected leg, leading to atrophy of leg muscles). Thus, the healthcare provider may also examine additional body parts of the patient for evidence of atrophy of or injury to surrounding ligaments, tendons, bones, and muscles, examples of muscles being such as quadriceps, hamstrings, or calf muscle groups of the leg with the knee injury. The healthcare provider may also obtain information as to a pain level of the patient before, during, and/or after the examination.

The healthcare provider can use the information obtained from the examination (e.g., the results of the examination) to determine a proper treatment plan for the patient. If the healthcare provider cannot conduct a physical examination of the one or more body parts of the patient, the healthcare provider may not be able to fully assess the patient's injury and the treatment plan may not be optimal. Accordingly, embodiments of the present disclosure pertain to systems and methods for conducting a remote examination of a patient. The remote examination system provides the healthcare provider with the ability to conduct a remote examination of the patient, not only by communicating with the patient, but by virtually observing and/or feeling the patient's one or more body parts.

In some embodiments, the systems and methods described herein may be configured for remote examination of a patient. For example, the systems and methods may be configured to use a treatment device configured to be manipulated by an individual while performing a treatment plan. The individual may include a user, patient, or other a person using the treatment device to perform various exercises for prehabilitation, rehabilitation, stretch training, and the like. The systems and methods described herein may be configured to use and/or provide a patient interface comprising an output device configured to present telemedicine information associated with a telemedicine session.

In some embodiments, the systems and methods described herein may be configured for remote examination of a patient. For example, the systems and methods may be configured to use a treatment device configured to be manipulated by a healthcare provider while the patient is performing a treatment plan. The systems and methods described herein may be configured to receive slave sensor data from the one or more slave sensors, use a manipulation of the master device to generate a manipulation instruction, transmit the manipulation instruction, and use the manipulation instruction to cause the slave pressure system to activate. Any or all of the methods described may be implemented during a telemedicine session or at any other desired time.

In some embodiments, the treatment devices may be communicatively coupled to a server. Characteristics of the patients, including the treatment data, may be collected before, during, and/or after the patients perform the treatment plans. For example, any or each of the personal information, the performance information, and the measurement information may be collected before, during, and/or after a patient performs the treatment plans. The results (e.g., improved performance or decreased performance) of performing each exercise may be collected from the treatment device throughout the treatment plan and after the treatment plan is performed. The parameters, settings, configurations, etc. (e.g., position of pedal, amount of resistance, etc.) of the treatment device may be collected before, during, and/or after the treatment plan is performed.

Each characteristic of the patient, each result, and each parameter, setting, configuration, etc. may be timestamped and may be correlated with a particular step or set of steps in the treatment plan. Such a technique may enable the determination of which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment devices and/or any suitable computing device (e.g., computing devices where personal information is entered, such as the interface of the computing device described herein, a clinician interface, patient interface, and the like) over time as the patients use the treatment devices to perform the various treatment plans. The data that may be collected may include the characteristics of the patients, the treatment plans performed by the patients, the results of the treatment plans, any of the data described herein, any other suitable data, or a combination thereof.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment device for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. In some embodiments, the artificial intelligence engine may be used to identify trends and/or patterns and to define new cohorts based on achieving desired results from the treatment plans and machine learning models associated therewith may be trained to identify such trends and/or patterns and to recommend and rank the desirability of the new cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment device while the new patient uses the treatment device to perform the treatment plan.

As may be appreciated, the characteristics of the new patient (e.g., a new user) may change as the new patient uses the treatment device to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion.

A different treatment plan may be selected for the new patient, and the treatment device may be controlled, distally (e.g., which may be referred to as remotely) and based on the different treatment plan, while the new patient uses the treatment device to perform the treatment plan. Such techniques may provide the technical solution of distally controlling a treatment device.

Further, the systems and methods described herein may lead to faster recovery times and/or better results for the patients because the treatment plan that most accurately fits their characteristics is selected and implemented, in real-time, at any given moment. "Real-time" may also refer to near real-time, which may be less than 10 seconds or any reasonably proximate difference between two different times. As described herein, the term "results" may refer to medical results or medical outcomes. Results and outcomes may refer to responses to medical actions. The term "medical action(s)" may refer to any suitable action performed by the medical professional, and such action or actions may include diagnoses, prescription of treatment plans, prescription of treatment devices, and the making, composing and/or executing of appointments, telemedicine sessions, prescription of medicines, telephone calls, emails, text messages, and the like.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may be trained to output treatment plans that are not optimal i.e., sub-optimal, nonstandard, or otherwise excluded (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient. In some embodiments, the artificial intelligence engine may monitor the treatment data received while the patient (e.g., the user) with, for example, high blood pressure, uses the treatment device to perform an appropriate treatment plan and may modify the appropriate treatment plan to include features of an excluded treatment plan that may provide beneficial results for the patient if the treatment data indicates the patient is handling the appropriate treatment plan without aggravating, for example, the high blood pressure condition of the patient. In some embodiments, the artificial intelligence engine may modify the treatment plan if the monitored data shows the plan to be inappropriate or counterproductive for the user.

In some embodiments, the treatment plans and/or excluded treatment plans may be presented, during a telemedicine or telehealth session, to a healthcare provider. The healthcare provider may select a particular treatment plan for the patient to cause that treatment plan to be transmitted to the patient and/or to control, based on the treatment plan, the treatment device. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment device.

In such cases, the recommended treatment plans and/or excluded treatment plans may be presented simultaneously with a video of the patient in real-time or near real-time during a telemedicine or telehealth session on a user interface of a computing device of a medical professional. The video may also be accompanied by audio, text and other multimedia information and/or other sensorial or perceptive (e.g., tactile, gustatory, haptic, pressure-sensing-based or electromagnetic (e.g., neurostimulation). Real-time may refer to less than or equal to 2 seconds. Near real-time may refer to any interaction of a sufficiently short time to enable two individuals to engage in a dialogue via such user interface, and will generally be less than 10 seconds (or any suitably proximate difference between two different times) but greater than 2 seconds.

Presenting the treatment plans generated by the artificial intelligence engine concurrently with a presentation of the patient video may provide an enhanced user interface because the healthcare provider may continue to visually and/or otherwise communicate with the patient while also reviewing the treatment plans on the same user interface. The enhanced user interface may improve the healthcare provider's experience using the computing device and may encourage the healthcare provider to reuse the user interface. Such a technique may also reduce computing resources (e.g., processing, memory, network) because the healthcare provider does not have to switch to another user interface screen to enter a query for a treatment plan to recommend based on the characteristics of the patient. The artificial intelligence engine may be configured to provide, dynamically on the fly, the treatment plans and excluded treatment plans.

In some embodiments, the treatment device may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare provider may adapt, remotely during a telemedicine session, the treatment device to the needs of the patient by causing a control instruction to be transmitted from a server to treatment device. Such adaptive nature may improve the results of recovery for a patient, furthering the goals of personalized medicine, and enabling personalization of the treatment plan on a per-individual basis.

FIGS. 1-11, discussed below, and the various embodiments used to describe the principles of this disclosure are by way of illustration only and should not be construed in any way to limit the scope of the disclosure.

FIG. 1 illustrates a high-level component diagram of an illustrative remote examination system 100 according to certain embodiments of this disclosure. In some embodiments, the remote examination system 100 may include a slave computing device 102 communicatively coupled to a slave device, such as a treatment device 106. The treatment device can include a slave sensor 108 and a slave pressure system 110. The slave pressure system can include a slave motor 112. The remote examination system may also be communicatively coupled to an imaging device 116. Each of the slave computing device 102, the treatment device 106, and the imaging device 116 may include one or more processing devices, memory devices, and network interface cards. The network interface cards may enable communication via a wireless protocol for transmitting data over short distances, such as Bluetooth, ZigBee, etc. In some embodiments, the slave computing device 102 is communicatively coupled to the treatment device 106 and the imaging device 116 via Bluetooth.

Additionally, the network interface cards may enable communicating data over long distances, and in one example, the slave computing device 102 may communicate with a network 104. The network 104 may be a public network (e.g., connected to the Internet via wired (Ethernet) or wireless (WiFi)), a private network (e.g., a local area network (LAN) or wide area network (WAN)), or a combination thereof. The slave computing device 102 may be communicatively coupled with one or more master computing devices 122 and a cloud-based computing system 142.

The slave computing device 102 may be any suitable computing device, such as a laptop, tablet, smartphone, or computer. The slave computing device 102 may include a display that is capable of presenting a user interface, such as a patient portal 114. The patient portal 114 may be implemented in computer instructions stored on the one or more memory devices of the slave computing device 102 and executable by the one or more processing devices of the slave computing device 102. The patient portal 114 may present various screens to a patient that enable the patient to view his or her medical records, a treatment plan, or progress during the treatment plan; to initiate a remote examination session; to control parameters of the treatment device 106; to view progress of rehabilitation during the remote examination session; or combination thereof. The slave computing device 102 may also include instructions stored on the one or more memory devices that, when executed by the one or more processing devices of the slave computing device 102, perform operations to control the treatment device 106.

The slave computing device 102 may execute the patient portal 114. The patient portal 114 may be implemented in computer instructions stored on the one or more memory devices of the slave computing device 102 and executable by the one or more processing devices of the slave computing device 102. The patient portal 114 may present various screens to a patient which enable the patient to view a remote examination provided by a healthcare provider, such as a physician or a physical therapist. The patient portal 114 may also provide remote examination information for a patient to view. The examination information can include a summary of the examination and/or results of the examination in real-time or near real-time, such as measured properties (e.g., angles of bend/extension, pressure exerted on the treatment device 106, images of the examined/treated body part, vital signs of the patient, such as heartrate, temperature, etc.) of the patient during the examination. The patient portal 114 may also provide the patient's health information, such as a health history, a treatment plan, and a progress of the patient throughout the treatment plan. So the examination of the patient may begin, the examination information specific to the patient may be transmitted via the network 104 to the cloud-based computing system 142 for storage and/or to the slave computing device 102.

The treatment device 106 may be an examination device for a body part of a patient. As illustrated in FIGS. 2A-D, the treatment device 106 can be configured in alternative arrangements and is not limited to the example embodiments described in this disclosure. Although not illustrated, the treatment device 106 can include a slave motor 112 and a motor controller 118. The treatment device 106 can include a slave pressure system 110. The slave pressure system 110 is any suitable pressure system configured to increase and/or decrease the pressure in the treatment device 106. For example, the slave pressure system 110 can comprise the slave motor 112, the motor controller 118, and a pump. The motor controller 118 can activate the slave motor 112 to cause a pump or any other suitable device to inflate or deflate one or more sections 210 of the treatment device 106. The treatment device 106 can be operatively coupled to one or more slave processing devices. The one or more slave processing devices can be configured to execute instructions in accordance with aspects of this disclosure.

Figure 2A:
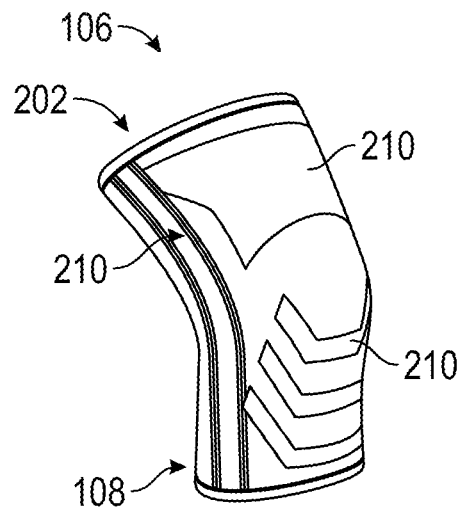
FIGS. 2A-D generally illustrate example treatment devices according to certain aspects of this disclosure.

As illustrated in FIG. 2A, the treatment device 106 may comprise a brace 202 (e.g., a knee brace) configured to fit on the patient's body part, such as an arm, a wrist, a neck, a torso, a leg, a knee, an ankle, hips, or any other suitable body part. The brace 202 may include slave sensors 108. The slave sensors 108 can be configured to detect information correlating with the patient. For example, the slave sensors 108 can detect a measured level of force exerted from the patient to the treatment device 106, a temperature of the one or more body parts in contact with the patient, a movement of the treatment device 106, any other suitable information, or any combination thereof. The brace 202 may include sections 210. The sections 210 can be formed as one or more chambers. The sections 210 may be configured to be filled with a liquid (e.g., a gel, air, water, etc.). The sections 210 may be configured in one or more shapes, such as, but not limited to rectangles, squares, diamonds circles, trapezoids, any other suitable shape, or combination thereof. The sections 210 may be the same or different sizes. The sections 210 may be positioned throughout the treatment device 106. The sections 210 can be positioned on the brace 202 above a knee portion, below the knee portion, and along the sides of the knee portion. In some embodiments, the brace 202 may include sections 210 positioned adjacent to each other and positioned throughout the brace 202. The sections 210 are not limited to the exemplary illustrations in FIG. 4. The brace 202 may include the one or more materials for the brace 202 and, in some embodiments, straps coupled to the brace 202. The brace 202 be formed from metal, foam, plastic, elastic, or any suitable material or combination of materials. The brace 202 may be formed in any suitable shape, size, or design.

Figure 2B:
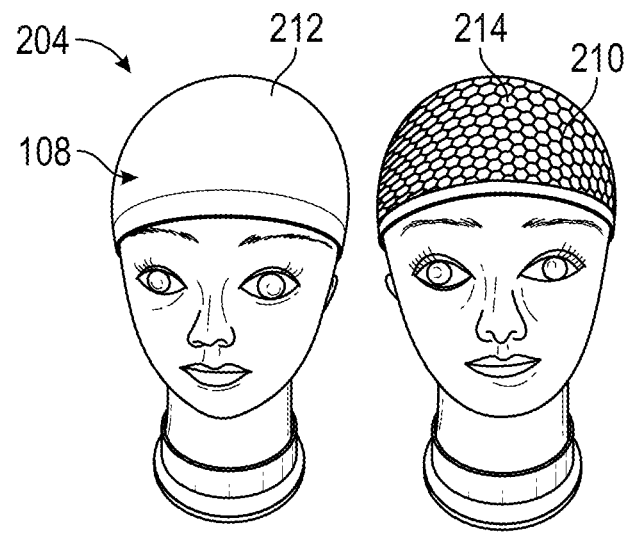

As illustrated in FIG. 2B, the treatment device 106 may comprise a cap 204 that can be configured to fit onto the patient's head. FIG. 2B illustrates exemplary layers of the treatment device 106. The treatment device 106 may include a first layer 212 and a second layer 214. The first layer may be an outer later and the second layer 214 may be an inner layer. The second layer 214 may include the sections 210 and one or more sensors 108. In this example embodiment, the sections 210 are coupled to and/or from portions of the second layer 214. The sections 210 can be configured in a honeycomb pattern. The one or more sensors 108 may be coupled to the first layer 212. The first layer 212 can be coupled to the second layer 214. The first layer 212 can be designed to protect the sections 210 and the sensors 108. The cap 204 may include a strap. The cap 204 and/or the strap be formed from metal, foam, plastic, elastic, or any suitable material or combination of materials. The cap 204 may be formed in any suitable shape, size, or design.

Figure 2C:
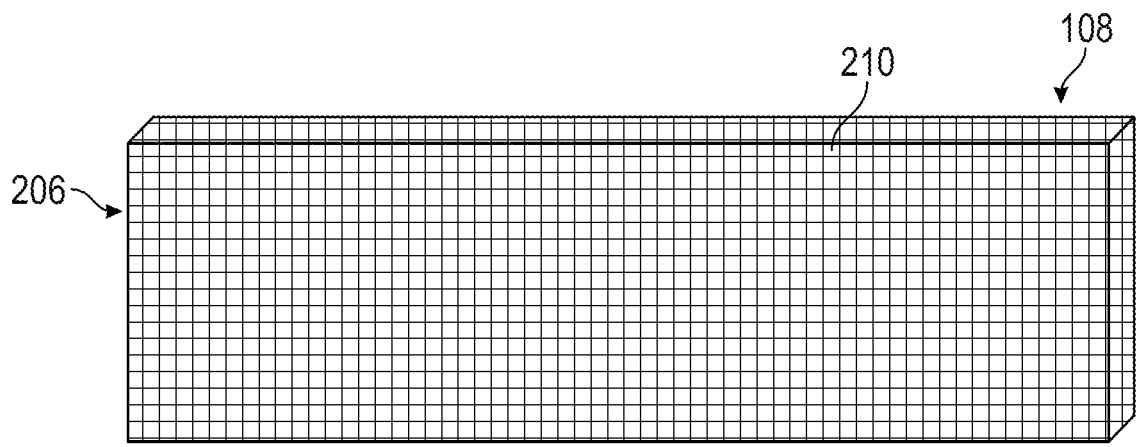

As illustrated in FIG. 2C, the slave may comprise a mat 206. The mat 206 may be configured for a patient to lie or sit down, or to stand upon. The mat 206 may include one or more sensors 108. The mat 206 may include one or more sections 210. The sections 210 in the treatment device 106 can be configured in a square grid pattern. The one or more sensors 108 may be coupled to and/or positioned within the one or more sections 210. The mat 206 can be rectangular, circular, square, or any other suitable configuration. The mat 206 be formed from metal, foam, plastic, elastic, or any suitable material or combination of materials. The mat 206 may include one or more layers, such as a top layer.

Figure 2D:
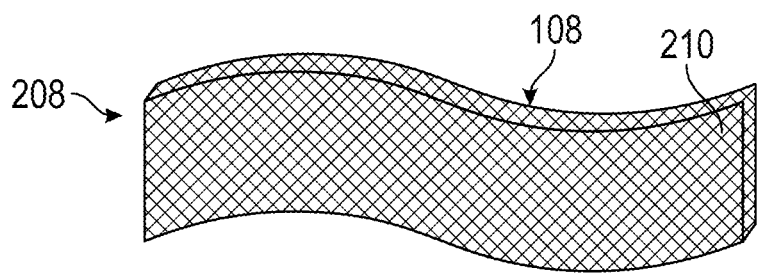

As illustrated in FIG. 2D, the treatment device 106 may comprise a wrap 208. The wrap 208 may be configured to wrap the wrap 208 around one or more portions and/or one or more body parts of the patient. For example, the wrap 208 may be configured to wrap around a person's torso. The wrap 208 may include one or more sensors 108. The wrap 208 may include one or more sections 210. The sections 210 in the treatment device 106 can be configured in a diamond grid pattern. The one or more sensors 108 may be coupled to and/or positioned within the one or more sections 210. The wrap 208 can be rectangular, circular, square, or any other suitable configuration. The wrap 208 may include a strap. The wrap 208 and/or the strap be formed from metal, foam, plastic, elastic, or any suitable material or combination of materials.

Figure 8:
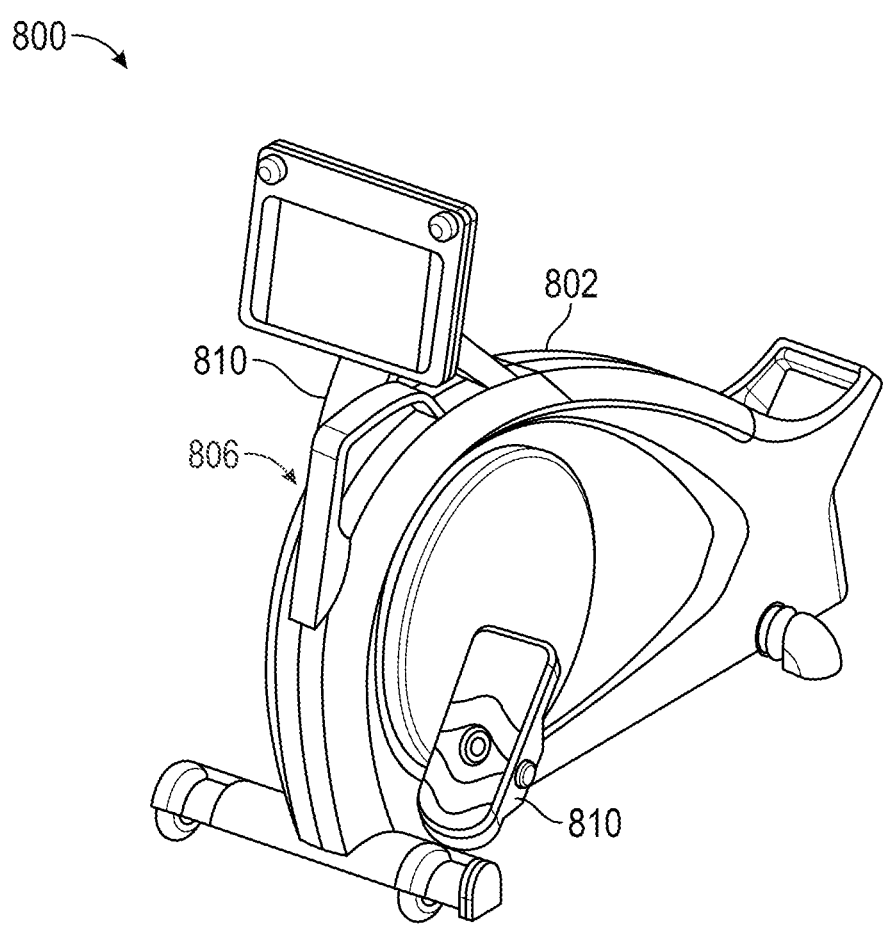
FIG. 8 generally illustrates a perspective view of an example of the device according to certain aspects of this disclosure.
Figure 9:
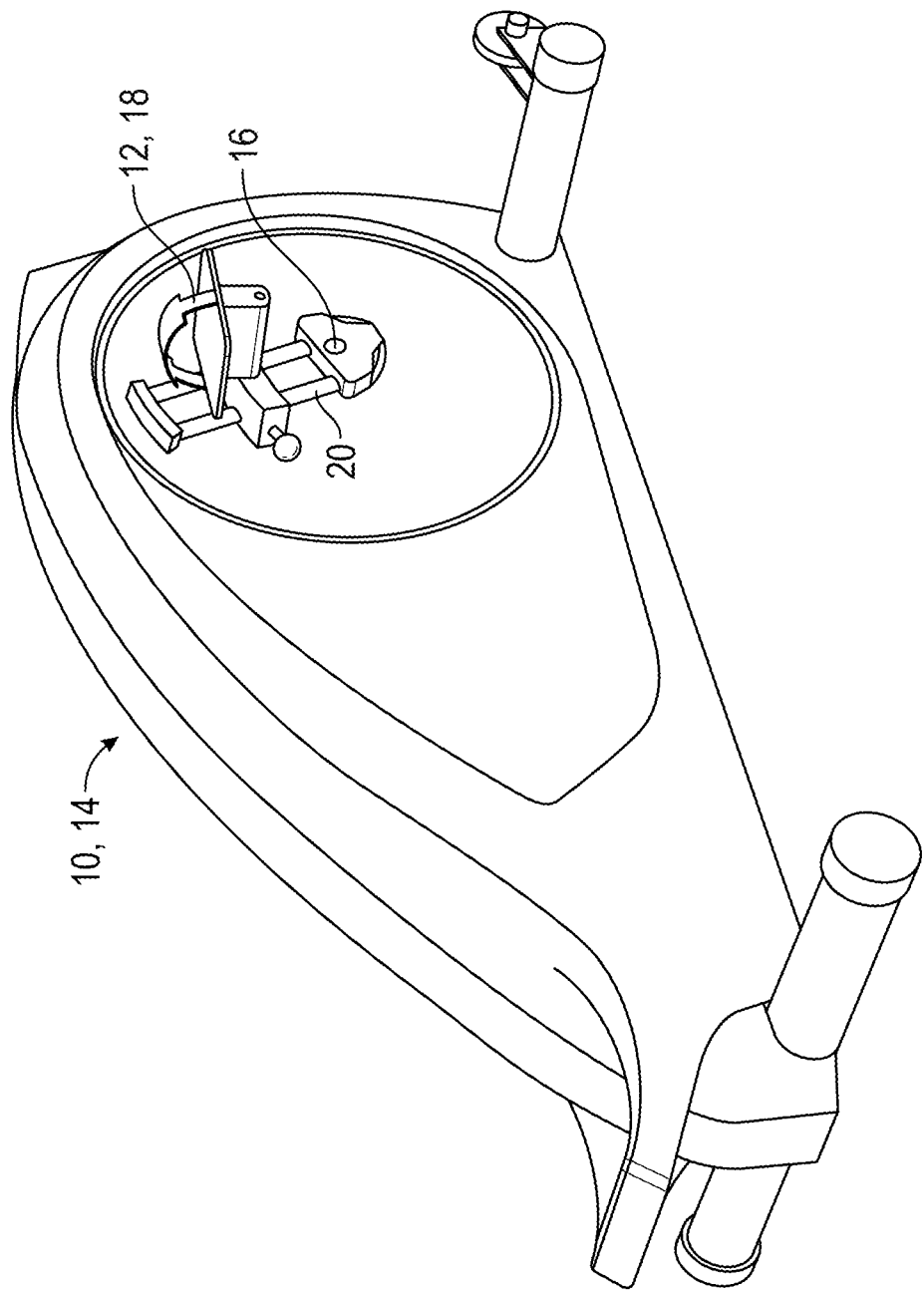
FIG. 9 generally illustrates a perspective view of an embodiment of the device, such as a treatment device according to certain aspects of this disclosure.
Figure 10:
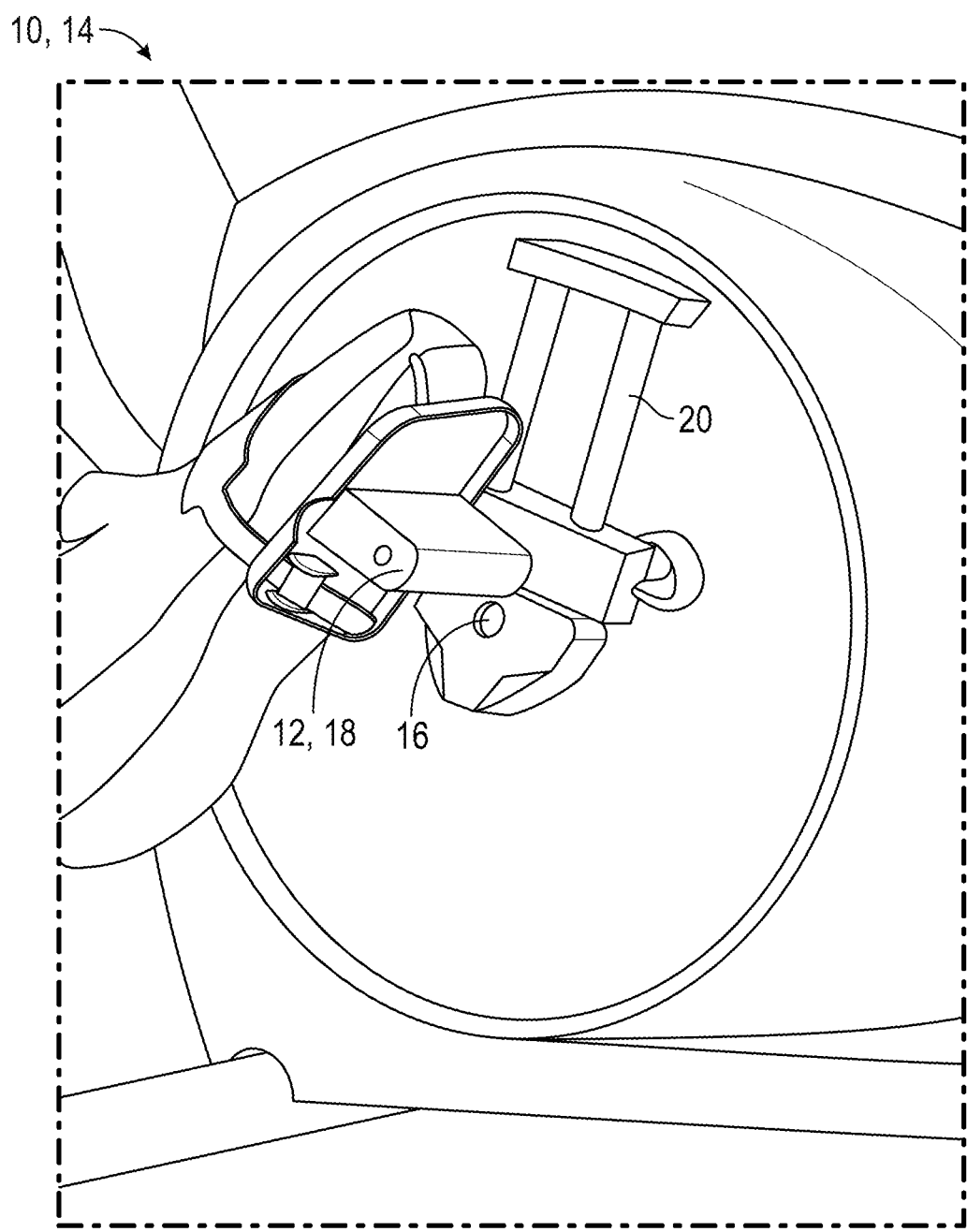
FIG. 10 generally illustrates a perspective view of a pedal of the treatment device of FIG. 9 according to certain aspects of this disclosure.

As illustrated in FIGS. 8-10, the treatment device may comprise an electromechanical device, such as a physical therapy device. FIG. 8 illustrates a perspective view of an example of a treatment device 800 according to certain aspects of this disclosure. Specifically, the treatment device 800 illustrated is an electromechanical device 802, such as an exercise and rehabilitation device (e.g., a physical therapy device or the like). The electromechanical device 802 is shown having pedal 810 on opposite sides that are adjustably positionable relative to one another on respective radially-adjustable couplings 808. The depicted electromechanical device 802 is configured as a small and portable unit so that it is easily transported to different locations at which rehabilitation or treatment is to be provided, such as at patients' homes, alternative care facilities, or the like. The patient may sit in a chair proximate the electromechanical device 802 to engage the electromechanical device 802 with the patient's feet, for example. The electromechanical device 802 includes a rotary device such as radially-adjustable couplings 808 or flywheel or the like rotatably mounted such as by a central hub to a frame or other support. The pedals 810 are configured for interacting with a patient to be rehabilitated and may be configured for use with lower body extremities such as the feet, legs, or upper body extremities, such as the hands, arms, and the like. For example, the pedal 810 may be a bicycle pedal of the type having a foot support rotatably mounted onto an axle with bearings. The axle may or may not have exposed end threads for engaging a mount on the radially-adjustable coupling 808 to locate the pedal on the radially-adjustable coupling 808. The radially-adjustable coupling 808 may include an actuator configured to radially adjust the location of the pedal to various positions on the radially-adjustable coupling 808.

Alternatively, the radially-adjustable coupling 808 may be configured to have both pedals 810 on opposite sides of a single coupling 808. In some embodiments, as depicted, a pair of radially-adjustable couplings 808 may be spaced apart from one another but interconnected by the electric motor 806. In the depicted example, the computing device 102 may be mounted on the frame of the electromechanical device 802 and may be detachable and held by the user while the user operates the electromechanical device 802. The computing device 102 may present the patient portal 114 and control the operation of the electric motor 806, as described herein.

In some embodiments, as described in U.S. Pat. No. 10,173,094 (U.S. application Ser. No. 15/700,293), which is incorporated by reference herein in its entirety for all purposes, the device 106 may take the form of a traditional exercise/rehabilitation device which is more or less non-portable and remains in a fixed location, such as a rehabilitation clinic or medical practice. The device 106 may include a seat and be less portable than the device 106 shown in FIG. 8. FIG. 8 is not intended to be limiting: the treatment device 800 may include more or fewer components than those illustrated in FIG. 8.

FIGS. 9-10 generally illustrate an embodiment of a treatment device, such as a treatment device 10. More specifically, FIG. 9 generally illustrates a treatment device 10 in the form of an electromechanical device, such as a stationary cycling machine 14, which may be called a stationary bike, for short. The stationary cycling machine 14 includes a set of pedals 12 each attached to a pedal arm 20 for rotation about an axle 16. In some embodiments, and as generally illustrated in FIG. 9, the pedals 12 are movable on the pedal arm 20 in order to adjust a range of motion used by the patient in pedaling. For example, the pedals being located inwardly toward the axle 16 corresponds to a smaller range of motion than when the pedals are located outwardly away from the axle 16. A pressure sensor 18 is attached to or embedded within one of the pedals 12 for measuring an amount of force applied by the patient on the pedal 102. The pressure sensor 18 may communicate wirelessly to the treatment device 10 and/or to the patient interface 26. FIGS. 9-10 are not intended to be limiting: the treatment device 10 may include more or fewer components than those illustrated in FIGS. 9-10.

Figure 11:
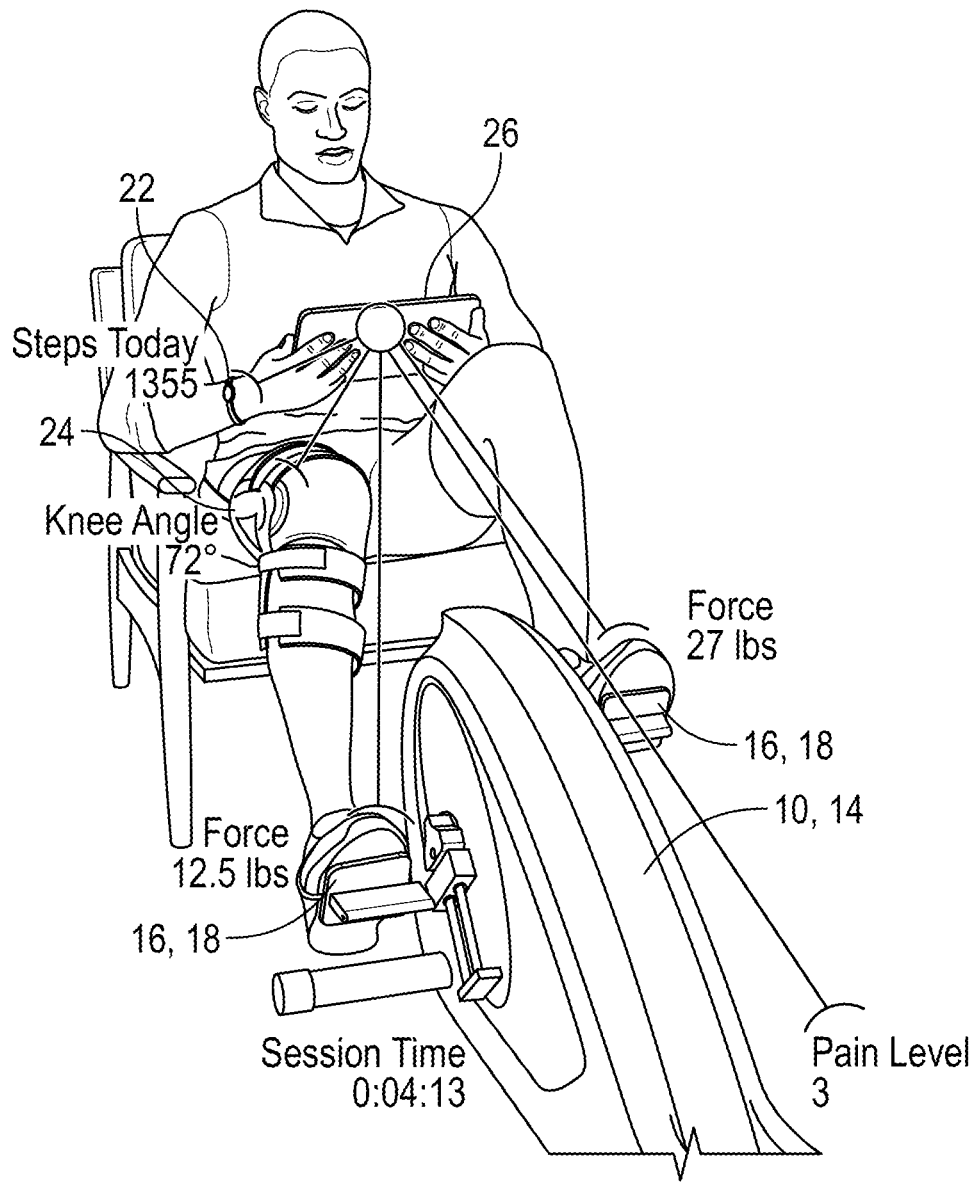
FIG. 11 generally illustrates a perspective view of a person using the treatment device of FIG. 9 according to certain aspects of this disclosure.

FIG. 11 generally illustrates a person (a patient) using the treatment device of FIG. 9, and showing sensors and various data parameters connected to a patient interface 26. The example patient interface 26 is a tablet computer or smartphone, or a phablet, such as an iPad, an iPhone, an Android device, or a Surface tablet, which is held manually by the patient. In some other embodiments, the patient interface 26 may be embedded within or attached to the treatment device 10. FIG. 11 generally illustrates the patient wearing the ambulation sensor 22 on his wrist, with a note showing "STEPS TODAY 1355", indicating that the ambulation sensor 22 has recorded and transmitted that step count to the patient interface 26. FIG. 11 also generally illustrates the patient wearing the goniometer 24 on his right knee, with a note showing "KNEE ANGLE 72°", indicating that the goniometer 24 is measuring and transmitting that knee angle to the patient interface 26. FIG. 11 generally illustrates a right side of one of the pedals 12 with a pressure sensor 18 showing "FORCE 12.5 lbs.", indicating that the right pedal pressure sensor 18 is measuring and transmitting that force measurement to the patient interface 26. FIG. 11 also generally illustrates a left side of one of the pedals 12 with a pressure sensor 18 showing "FORCE 27 lbs.", indicating that the left pedal pressure sensor 18 is measuring and transmitting that force measurement to the patient interface 26. FIG. 11 also generally illustrates other patient data, such as an indicator of "SESSION TIME 0:04:13", indicating that the patient has been using the treatment device 10 for 4 minutes and 13 seconds. This session time may be determined by the patient interface 26 based on information received from the treatment device 10. FIG. 11 also generally illustrates an indicator showing "PAIN LEVEL 3". Such a pain level may be obtained from the patient in response to a solicitation, such as a question, presented upon the patient interface 26. The treatment device 106 may include at least one or more motor controllers 118 and one or more motors 112, such as an electric motor. A pump, not illustrated, may be operatively coupled to the motor. The pump may be a hydraulic pump or any other suitable pump. The pump may be configured to increase or decrease pressure within the treatment device 106. The size and speed of the pump may determine the flow rate (i.e., the speed that the load moves) and the load at the slave motor 112 may determine the pressure in one or more sections 210 of the treatment device 106. The pump can be activated to increase or decrease pressure in the one or more sections 210. One or more of the sections 210 may include a sensor 108. The sensor 108 can be a sensor for detecting signals, such as a measured level of force, a temperature, or any other suitable signal. The motor controller 118 may be operatively coupled to the motor 112 and configured to provide commands to the motor 112 to control operation of the motor 112. The motor controller 118 may include any suitable microcontroller including a circuit board having one or more processing devices, one or more memory devices (e.g., read-only memory (ROM) and/or random access memory (RAM)), one or more network interface cards, and/or programmable input/output peripherals. The motor controller 118 may provide control signals or commands to drive the motor 112. The motor 112 may be powered to drive the pump of the treatment device 106. The motor 112 may provide the driving force to the pump to increase or decrease pressure at configurable speeds. Further, the treatment device 106 may include a current shunt to provide resistance to dissipate energy from the motor 112. In some embodiments, the treatment device 106 may comprise a haptic system, a pneumatic system, any other suitable system, or combination thereof. For example, the haptic system can include a virtual touch by applying forces, vibrations, or motions to the patient through the treatment device 106.

The slave computing device 102 may be communicatively connected to the treatment device 106 via a network interface card on the motor controller 118. The slave computing device 102 may transmit commands to the motor controller 118 to control the motor 112. The network interface card of the motor controller 118 may receive the commands and transmit the commands to the motor 112 to drive the motor 112. In this way, the slave computing device 102 is operatively coupled to the motor 112.

The slave computing device 102 and/or the motor controller 118 may be referred to as a control system (e.g., a slave control system) herein. The patient portal 114 may be referred to as a patient user interface of the control system. The control system may control the motor 112 to operate in a number of modes: standby, inflate, and deflate. The standby mode may refer to the motor 112 powering off so it does not provide a driving force to the one or more pumps. For example, if the pump does not receive instructions to inflate or deflate the treatment device 106, the motor 112 may remain turned off. In this mode, the treatment device 106 may not provide additional pressure to the patient's body part(s).

The inflate mode may refer to the motor 112 receiving manipulation instructions comprising measurements of pressure, causing the motor 112 to drive the one or more pumps coupled to the one or more sections of the treatment device 106 to inflate the one or more sections. The manipulation instruction may be configurable by the healthcare provider. For example, as the healthcare provider moves a master device 126, the movement is provided in a manipulation instruction for the motor 112 to drive the pump to inflate one or more sections of the treatment device 106. The manipulation instruction may include a pressure gradient to inflate first and second sections in a right side of a knee brace to first and second measured levels of force and inflate a third section in a left side of the knee brace to a third measured level of force. The first measured level of force correlates with the amount of pressure applied to the master device 126 by the healthcare provider's first finger. The second measured level of force correlates with the amount of pressure applied to the master device 126 by the healthcare provider's second finger. The third measured level of force correlates with the amount of pressure applied to the master device 126 by the healthcare provider's third finger.

The deflation mode may refer to the motor 112 receiving manipulation instructions comprising measurements of pressure, causing the motor 112 to drive the one or more pumps coupled to the one or more sections of the treatment device 106 to deflate the one or more sections. The manipulation instruction may be configurable by the healthcare provider. For example, as the healthcare provider moves the master device 126, the movement is provided in a manipulation instruction for the motor 112 to drive the pump to deflate one or more sections of the treatment device 106. The manipulation instruction may include a pressure gradient to deflate the first and second sections in the right side of the knee brace to fourth and fifth measured levels of force and deflate the third section in the left side of the knee brace to the third measured level of force. The fourth measured level of force correlates with the amount of pressure applied to the master device 126 by the healthcare provider's first finger. The fifth measured level of force correlates with the amount of pressure applied to the master device 126 by the healthcare provider's second finger. The sixth measured level of force correlates with the amount of pressure applied to the master device 126 by the healthcare provider's third finger. In this example, the healthcare provider loosened a grip (e.g., applied less pressure to each of the three fingers) applied to the treatment device 106 virtually via the master device 126.

During one or more of the modes, the one or more slave sensors 108 may measure force (i.e., pressure or weight) exerted by a part of the body of the patient. For example, the each of the one or more sections 310 of the treatment device 106 may contain any suitable sensor (e.g., strain gauge load cell, piezoelectric crystal, hydraulic load cell, etc.) for measuring force exerted on the treatment device 106. Further, the each of the one or more sections 310 of the treatment device 106 may contain any suitable sensor for detecting whether the body part of the patient separates from contact with the treatment device 106. The force detected may be transmitted via the network interface card of the treatment device 106 to the control system (e.g., slave computing device 102 and/or the slave controller 118). As described further below, the control system may modify a parameter of operating the slave motor 112 using the measured force. Further, the control system may perform one or more preventative actions (e.g., locking the slave motor 112 to stop the pump from activating, slowing down the slave motor 112, presenting a notification to the patient such as via the patient portal 114, etc.) when the body part is detected as separated from the treatment device 106, among other things.

In some embodiments, the remote examination system 100 includes the imaging device 116. The imaging device 116 may be configured to capture and/or measure angles of extension and/or bend of body parts and transmit the measured angles to the slave computing device 102 and/or the master computing device 122. The imaging device 116 may be included in an electronic device that includes the one or more processing devices, memory devices, and/or network interface cards. The imaging device 116 may be disposed in a cavity of the treatment device 106 (e.g., in a mechanical brace). The cavity of the mechanical brace may be located near a center of the mechanical brace such that the mechanical brace affords to bend and extend. The mechanical brace may be configured to secure to an upper body part (e.g., leg, arm, etc.) and a lower body part (e.g., leg, arm, etc.) to measure the angles of bend as the body parts are extended away from one another or retracted closer to one another.

The imaging device 116 can be a wristband. The wristband may include a 2-axis accelerometer to track motion in the X, Y, and Z directions, an altimeter for measuring altitude, and/or a gyroscope to measure orientation and rotation. The accelerometer, altimeter, and/or gyroscope may be operatively coupled to a processing device in the wristband and may transmit data to the processing device. The processing device may cause a network interface card to transmit the data to the slave computing device 102 and the slave computing device 102 may use the data representing acceleration, frequency, duration, intensity, and patterns of movement to track measurements taken by the patient over certain time periods (e.g., days, weeks, etc.). Executing a clinical portal 134, the slave computing device 102 may transmit the measurements to the master computing device 122. Additionally, in some embodiments, the processing device of the wristband may determine the measurements taken and transmit the measurements to the slave computing device 102. In some embodiments, the wristband may use photoplethysmography (PPG), which detects an amount of red light or green light on the skin of the wrist, to measure heartrate. For example, blood may absorb green light so that when the heart beats, the blood flow may absorb more green light, thereby enabling the detection of heartrate. The heartrate may be sent to the slave computing device 102 and/or the master computing device 122.

The slave computing device 102 may present the measurements (e.g., measured level of force or temperature) of the body part of the patient taken by the treatment device 106 and/or the heartrate of the patient via a graphical indicator (e.g., a graphical element) on the patient portal 114, as discussed further below. The slave computing device 102 may also use the measurements and/or the heart rate to control a parameter of operating the treatment device 106. For example, if the measured level of force exceeds a target pressure level for an examination session, the slave computing device 102 may control the motor 112 to reduce the pressure being applied to the treatment device 106.

In some embodiments, the remote examination system 100 may include a master computing device 122 communicatively coupled to a master console 124. The master console 124 can include a master device 126. The master device 126 can include a master sensor 128 and a master pressure system 130. The master pressure system can include a master motor 132. The remote examination system may also be communicatively coupled to a master display 136. Each of the master computing device 122, the master device 126, and the master display 136 may include one or more processing devices, memory devices, and network interface cards. The network interface cards may enable communication via a wireless protocol for transmitting data over short distances, such as Bluetooth, ZigBee, Near-Field Communications (NFC), etc. In some embodiments, the master computing device 122 is communicatively coupled to the master device 126 and the master display 136 via Bluetooth.

Additionally, the network interface cards may enable communicating data over long distances, and in one example, the master computing device 122 may communicate with a network 104. The master computing device 122 may be communicatively coupled with the slave computing device 102 and the cloud-based computing system 142.

The master computing device 122 may be any suitable computing device, such as a laptop, tablet, smartphone, or computer. The master computing device 122 may include a display capable of presenting a user interface, such as a clinical portal 134. The clinical portal 134 may be implemented in computer instructions stored on the one or more memory devices of the master computing device 122 and executable by the one or more processing devices of the master computing device 122. The clinical portal 134 may present various screens to a user (e.g., a healthcare provider), the screens configured to enable the user to view a patient's medical records, a treatment plan, or progress during the treatment plan; to initiate a remote examination session; to control parameters of the master device 126; to view progress of rehabilitation during the remote examination session, or combination thereof. The master computing device 122 may also include instructions stored on the one or more memory devices that, when executed by the one or more processing devices of the master computing device 122, perform operations to control the master device 126.

The master computing device 122 may execute the clinical portal 134. The clinical portal 134 may be implemented in computer instructions stored on the one or more memory devices of the master computing device 122 and executable by the one or more processing devices of the master computing device 122. The clinical portal 134 may present various screens to a healthcare provider (e.g., a clinician), the screens configured to enables the clinician to view a remote examination of a patient, such as a patient rehabilitating from a surgery (e.g., knee replacement surgery) or from an injury (e.g., sprained ankle). During a telemedicine session, an augmented image representing one or more body parts of the patient may be presented simultaneously with a video of the patient on the clinical portal 134 in real-time or in near real-time. For example, the clinical portal 134 may, at the same time, present the augmented image 402 of the knee of the patient and portions of the patient's leg extending from the knee and a video of the patient's upper body (e.g., face), so the healthcare provider can engage in more personal communication with the patient (e.g., via a video call). The video may be of the patient's full body, such that, during the telemedicine session, the healthcare provider may view the patient's entire body. The augmented image 402 can be displayed next to the video and/or overlaid onto the respective one or more body parts of the patient. For example, the augmented image 402 may comprise a representation of the treatment device 106 coupled to the patient's knee and leg portions. The clinical portal 134 may display the representation of the treatment device 106 overlaid onto the respective one or more body parts of the patient. Real-time may refer to less than 2 seconds, or any other suitable amount of time. Near real-time may refer to 2 or more seconds. The video may also be accompanied by audio, text, and other multimedia information. The master display 136 may also be configured to present the augmented image and/or the video as described herein.

Presenting the remote examination generated by the artificial intelligence engine concurrently with a presentation of the patient video may provide an enhanced user interface because the healthcare provider, while reviewing the examination on the same user interface, may also continue to visually and/or otherwise communicate with the patient. The enhanced user interface may improve the healthcare provider's experience in using the computing device and may encourage the healthcare provider to reuse the user interface. Such a technique may also reduce computing resources (e.g., processing, memory, network), because the healthcare provider does not have to switch to another user interface screen and, using the characteristics of the patient, enter a query for examination guidelines to recommend. For example, the enhanced user interface may provide the healthcare provider with recommended procedures to conduct during the telemedicine session. The recommended procedures may comprise a guide map, including indicators of locations and measured amounts of pressure to apply on the patient's one or more body parts. The artificial intelligence engine may analyze the examination results (e.g., measured levels of force exerted to and by the patient's one or more body parts, the temperature of the patient, the pain level of the patient, a measured range of motion of the one or more body parts, etc.) and provide, dynamically on the fly, the optimal examination procedures and excluded examination procedures.

The clinical portal 134 may also provide examination information generated during the telemedicine session for the healthcare provider to view. The examination information can include a summary of the examination and/or the results of the examination in real-time or near real-time, such as measured properties of the patient during the examination. Examples of the measured properties may include, but are not limited to, angles of bend/extension, pressure exerted on the master device 126, pressure exerted by the patient on the treatment device 106, images of the examined/treated body part, and vital signs of the patient, such as heartrate and temperature. The clinical portal 134 may also provide the clinician's notes and the patient's health information, such as a health history, a treatment plan, and a progress of the patient throughout the treatment plan. So the healthcare provider may begin the remote examination, the examination information specific to the patient may be transmitted via the network 104 to the cloud-based computing system 142 for storage and/or to the master computing device 122.

In some embodiments, the clinical portal 134 may include a treatment plan that includes one or more examination procedures (e.g., manipulation instructions to manipulate one or more sections 210 of the treatment device 106). For example, a healthcare provider may input, to the clinical portal 134, a treatment plan with pre-determined manipulation instructions for the treatment device 106 to perform during the remote examination. The healthcare provider may input the pre-determined manipulation instructions prior the remote examination. The treatment device 106 can be activated to perform the manipulations in accordance with the pre-determined manipulation instructions. The healthcare provider may observe the remote examination in real-time and make modifications to the pre-determined manipulation instructions during the remote examination. Additionally, the system 100 can store the results of the examination and the healthcare provider can complete the examination using the stored results (e.g., stored slave sensor data) and the master device 126. In other words, the master processing device can use the slave sensor data to manipulate the master device 126. This manipulation of the master device 126 can allow the healthcare provider to virtually feel the patient's one or more body parts and provide the healthcare provider with additional information to determine a personalized treatment plan for the patient.

The master device 126 may be an examination device configured for control by a healthcare provider. The master device 126 may be a joystick, a model treatment device (e.g., a knee brace to fit over a manikin knee), an examination device to fit over a body part of the healthcare provider (e.g., a glove device), any other suitable device, or combination thereof. The joystick may be configured to be used by a healthcare provider to provide manipulation instructions. The joystick may have one or more buttons (e.g., a trigger) to apply more or less pressure to one or more sections of the treatment device 106. The joystick may be configured to control a moveable indicator (e.g., a cursor) displayed at the master display or any other suitable display. The moveable indicator can be moved over an augmented image 400 of the treatment device 106 and/or one or more body parts of the patient. The healthcare provider may be able to provide verbal commands to increase and/or decrease pressure based on where the moveable indicator is positioned relative to the augmented image 400. The joystick may have master sensors 128 within a stick of the joystick. The stick may be configured to provide feedback to the user (e.g., vibrations or pressure exerted by the stick to the user's hand).

The model of the treatment device may be formed similarly to the treatment device 106. For example, if the treatment device 106 is the knee brace 202, the master device can be a model knee brace with similar characteristics of the knee brace 202. The model can be configured for coupling to a manikin or any other suitable device. The model can comprise the master pressure system 130 and master sensors 128 and function as described in this disclosure. The model may be configured for a healthcare provider to manipulate (e.g., touch, move, and/or apply pressure) to one or more sections of the model and to generate master sensor data based on such manipulations. The model can be operatively coupled to the treatment device 106. The master sensor data can be used to inflate and/or deflate one or more corresponding sections of the treatment device 106 (e.g., as the healthcare provider is manipulating the model, the treatment device 106 is being manipulated on the patient). Responsive to receiving the slave sensor data, the master pressure system 130 can active and inflate and/or deflate one or more sections of the model (e.g., the pressure applied to the treatment device 106 by the patient's one or more body parts is similarly applied to the model for the healthcare provider to examine). The healthcare provider can essentially feel, with his or her bare (or appropriately gloved) hands, the patient's one or more body parts (e.g., the knee) while the healthcare provider virtually manipulates the patient body part(s).

In some embodiments, the system 100 may include one or more master computing devices 122 and one or more master consoles 124. For example, a second master console can include a second master device 126 operatively coupled to a second master computing device. The second master device can comprise a second master pressure system 130, and, using the slave force measurements, the one or more processing devices of system 100 can be configured to activate the second master pressure system 130. During and/or after a telemedicine session, one or more healthcare providers can manipulate the treatment device 106 and/or use the slave sensor data to virtually feel the one or more body parts of the patient. For example, a physician and a physical therapist may virtually feel the one or more body parts of the patient at the same time or at different times. The physician may provide the manipulation instructions and the physical therapist may observe (e.g., virtually see and/or feel) how the patient's one or more body parts respond to the manipulations. The physician and the physical therapist may use different examination techniques (e.g., locations of the manipulations and/or measure levels of force applied to the treatment device 106) to obtain information for providing a treatment plan for the patient. Resulting from the physician using the master device 106 and the physical therapist using the second master device, each can provide manipulation instructions to the treatment device 106. The manipulation instructions from the master device 106 and the second master device may be provided at the same time or at a different time (e.g., the physician provides a first manipulation instruction via the master device 126 and the physical therapist provides a second manipulation instruction via the second master device). In another example, the physician may have input a pre-determined manipulation instruction for the remote examination and the physical therapist may use the second master device to adjust the pre-determined manipulation instructions. The physician and the physical therapist may be located remotely from each other (and remotely from the patient) and each can use the system 100 to examine the patient and provide a personalized treatment plan for the patient. The system 100 can allow for collaboration between one or more healthcare providers and provide the healthcare providers with information to make optimal adjustments to the patient's treatment plan.

Figure 3:
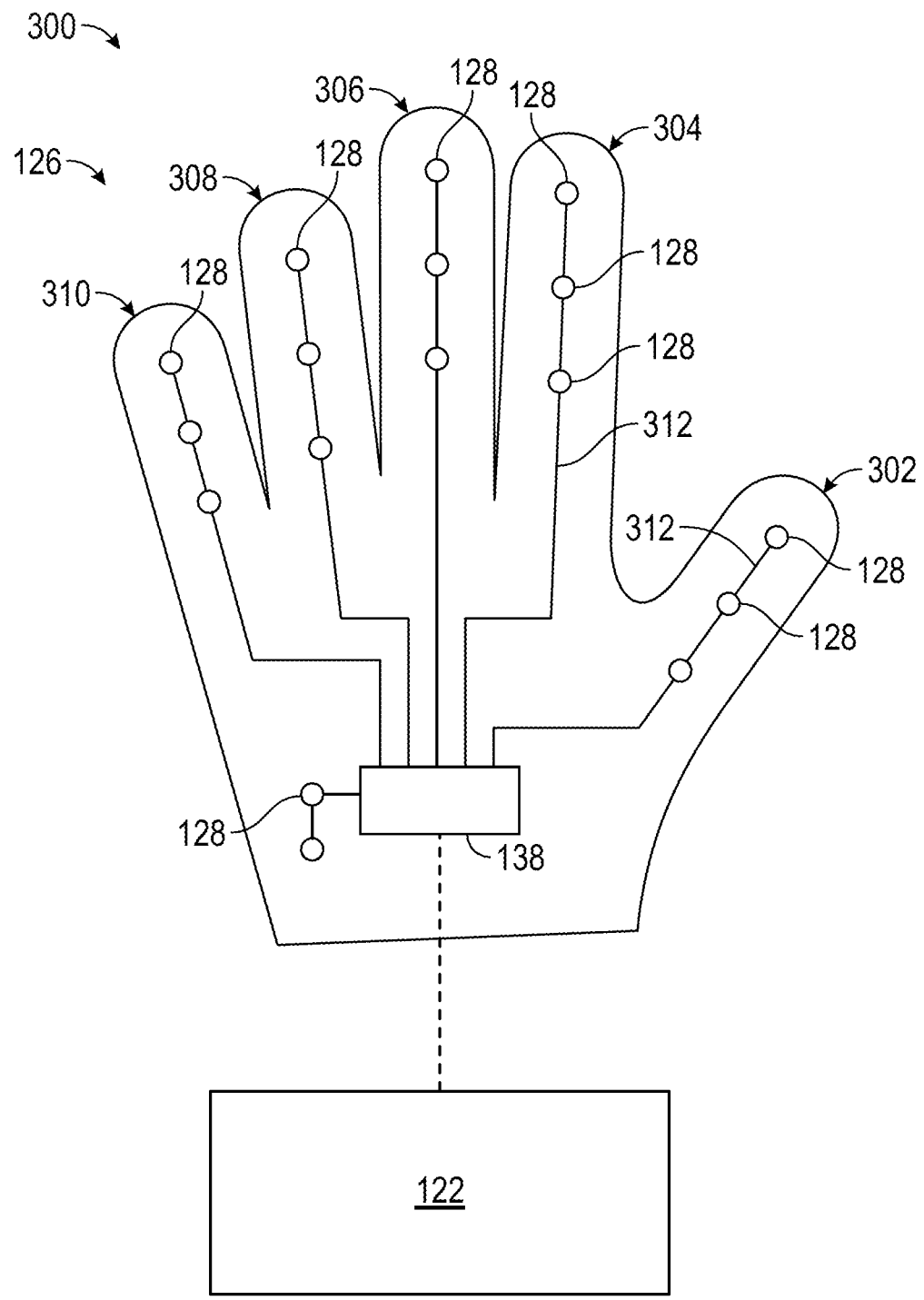
FIG. 3 generally illustrates an example master device according to certain aspects of this disclosure.

As illustrated in FIG. 3, the master device 126 comprises a glove device 300 configured to fit on a healthcare provider's hand. The glove device 300 can include fingers 302. The glove may include one or more sensors (e.g., one or more master sensors 128). The glove device 300 may include the master sensors 128 positioned along the fingers 302, 304, 306, 308, 310 (collectively, fingers 302), throughout the palm of the glove, in any other suitable location, or in any combination thereof. For example, each finger can include a series of master sensors 128 positioned along the fingers 302. Each of the series of master sensors 128 can be operatively coupled to one or more master controllers 138. The master device 126 may include at least one or more master controllers 138 and one or more master motors 132, such as an electric motor (not illustrated).

A pump (not illustrated) may be operatively coupled to the motor. The pump may be configured to increase or decrease pressure within the master device 126. The master device 126 may include one or more sections and the pump can be activated to increase or decrease pressure (e.g., inflating or deflating fluid, such as water, gel, air) in the one or more sections (e.g., one or more fingertips). One or more of the sections may include a master sensor 128. The master sensor 128 can be a sensor for detecting signals, such as pressure, or any other suitable signal. The master controller 138 may be operatively coupled to the master motor 132 and configured to provide commands to the master motor 132 to control operation of the master motor 132. The master controller 138 may include any suitable microcontroller including a circuit board having one or more processing devices, one or more memory devices (e.g., read-only memory (ROM) and/or random access memory (RAM)), one or more network interface cards, and/or programmable input/output peripherals. The master controller 138 may provide control signals or commands to drive the master motor 132. The master motor 132 may be powered to drive the pump of the master device 126. The master motor 132 may provide the driving force to the pump to increase or decrease pressure at configurable speeds. Further, the master device 126 may include a current shunt to provide resistance to dissipate energy from the master motor 132. In some embodiments, the treatment device 106 may comprise a haptic system, a pneumatic system, any other suitable system, or combination thereof. For example, the haptic system can include a virtual touch by applying forces, vibrations, or motions to the healthcare provider through the master device 126.

The master computing device 122 may be communicatively connected to the master device 126 via a network interface card on the master controller 138. The master computing device 122 may transmit commands to the master controller 138 to control the master motor 132. The network interface card of the master controller 138 may receive the commands and transmit the commands to the master controller 138 to drive the master motor 132. In this way, the master computing device 122 is operatively coupled to the master motor 132.

The master computing device 122 and/or the master controller 138 may be referred to as a control system (e.g., a master control system) herein. The clinical portal 134 may be referred to as a clinical user interface of the control system. The master control system may control the master motor 132 to operate in a number of modes, including: standby, inflate, and deflate. The standby mode may refer to the master motor 132 powering off so that it does not provide any driving force to the one or more pumps. For example, when the healthcare provider is not touching an augmented image of the treatment device 106, the pump of the master device 126 may not receive instructions to inflate or deflate one or more sections of the master device 126 and the master motor 132 may remain turned off. In the standby mode, the master device 126 may not apply pressure to the healthcare provider's body part(s) (e.g., to the healthcare provider's finger 304 via the glove device 300) because the healthcare provider is not in virtual contact with the treatment device 106. Furthermore, in standby mode, the master device 126 may not transmit the master sensor data based on manipulations of the master device 126 (e.g., pressure virtually exerted from the healthcare care provider's hand to the master device 126) to the patient via the treatment device 106.

The inflate mode may refer to the master motor 132 receiving slave sensor data comprising measurements of pressure, causing the master motor 132 to drive the one or more pumps coupled to the one or more sections of the master device 126 (e.g., one or more fingers 302, 304, 406, 308, 310) to inflate the one or more sections. The slave sensor data may be provided by the one or more slave sensors 108 of the treatment device 106 via the slave computing device 102. For example, as the healthcare provider manipulates (e.g., moves) the master device 126 to virtually contact one or more body parts of the patient using the treatment device 106 in contact with the patient's one or more body parts, the treatment device 106 is manipulated. The slave sensors 108 are configured to detect the manipulation of the treatment device 106. The detected information may include how the patient's one or more body parts respond to the manipulation. The one or more slave sensors 108 may detect that one area of the patient's body part exerts a first measured level of force and that another area of the patient's body part exerts a second measured level of force (e.g., the one area may be swollen or inconsistent with baseline measurements or expectations as compared to the other area). The master computing device 122 can receive the information from the slave sensor data and instruct the master motor 132 to drive the pump to inflate one or more sections of the master device 126. The level of inflation of the one or more sections of the master device 126 may correlate with one or more measured levels of force detected by the treatment device 106. The slave sensor data may include a pressure gradient. The master computing device 122 may instruct the master pressure system 130 to inflate a first section (e.g., the fingertips of the first finger 302) correlating with the first measured level of force exerted from a left side of the knee brace 202. The master computing device 122 may instruct the master pressure system 130 to inflate second and third sections (e.g., the fingertips of second and third fingers 304, 306) correlating with second and third measured levels of force exerted from a front side of the knee brace 202. In other words, in response to the master device 126 virtually touching the treatment device 106, the first measured level of force may correlate with the amount of pressure applied to the healthcare provider's first finger through the first finger 302 of the master device 126.

Similarly, the second measured level of force may correlate with the amount of measured force applied by the healthcare provider's second finger through the second finger 304 of the master device 126. The third measured level of force may correlate with the amount of measured force applied by the healthcare provider's third finger through the third finger 306 of the master device 126. The glove device 300 can include a fourth finger 308 to provide a fourth measured level of force, a fifth finger 310 to provide a fifth measured level of force, and/or other sections, such as a palm, or any combination thereof configured to provide measured levels of force to the healthcare provider. The sections of the glove device 300 can be inflated or deflated to correlate with the same and/or different levels of measured force exerted on the treatment device 106.

The deflation mode may refer to the master motor 132 receiving slave sensor data comprising measurements of pressure, causing the master motor 132 to drive the one or more pumps coupled to the one or more sections of the master device 126 (e.g., one or more fingers 302) to deflate the one or more sections. The deflation mode of the master pressure system 130 can function similarly as the inflation mode; however, in the deflation mode, the master pressure system 130 deflates, rather than inflates, the one or more sections of the master device 126. For example, the one or more slave sensors 108 may detect that one area of the patient's body part exerts a first measured level of force and that another area of the patient's body part exerts a second measured level of force (e.g., the one area may be less swollen or less inconsistent with baseline measurements or expectations as compared to the other area). The master computing device 122 can receive the information from the slave sensor data and instruct the master motor 132 to drive the pump to deflate one or more sections of the master device 126. The level of deflation of the one or more sections of the master device 126 may correlate with one or more measured levels of force detected by the treatment device 106.

The measured levels of force can be transmitted between the treatment device 106 and the master device 126 in real-time, near real-time, and/or at a later time. In other words, the healthcare provider can use the master device 126 to virtually examine the patient's body part using the healthcare provider's hand and feel the patient's body part (e.g., the pressure, etc.). Similarly, the patient can feel the healthcare provider virtually touching his or her body part (e.g., from the pressure exerted by the treatment device 106). During the telemedicine session, the patient, via the patient portal 114, can communicate to the healthcare provider via the clinical portal 134. For example, during the remote examination, the patient can inform the healthcare provider that the location of the body part that the healthcare provider is virtually touching (e.g., manipulating), is painful. The information can be communicated verbally and/or visually (e.g., input into the patient portal 114 directly by the client and transmitted to the clinical portal 134 and/or the master display 136). The healthcare provider can receive additional information, such as temperature of the patient's body part, vital signs of the patient, any other suitable information, or any combination thereof.

During one or more of the inflation and deflation modes, the one or more master sensors 128 may measure force (i.e., pressure) exerted by the healthcare provider via the master device 126. For example, one or more sections of the master device 126 may contain any suitable sensor (e.g., strain gauge load cell, piezoelectric crystal, hydraulic load cell, etc.) for measuring force exerted on the master device 126.

Further, each section 310 of the master device 126 may contain any suitable sensor for detecting whether the body part of the healthcare provider separates from contact with the master device 126. The measured level(s) of force detected may be transmitted via the network interface card of the master device 126 to the control system (e.g., master computing device 122 and/or the master controller 138). As described further below, using the measured level(s) of force, the control system may modify a parameter of operating the master motor 132. Further, the control system may perform one or more preventative actions (e.g., locking the master motor 132 to stop the pump from activating, slowing down the master motor 132, or presenting a notification to the healthcare provider (such as via the clinical portal 134, etc.)) when the body part is detected as being separated from the master device 126, among other things.

Figure 4A:
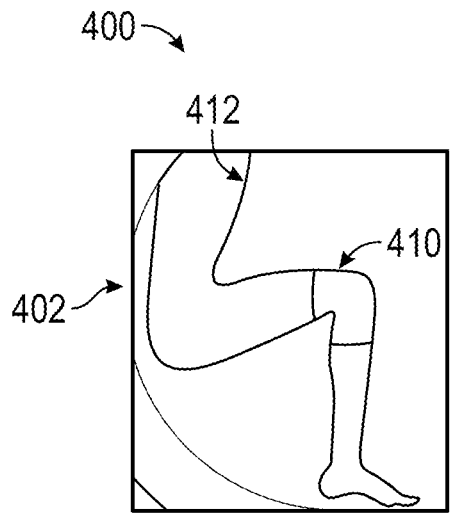
FIGS. 4A-D generally illustrate example augmented images according to certain aspects of this disclosure.
Figure 4B:
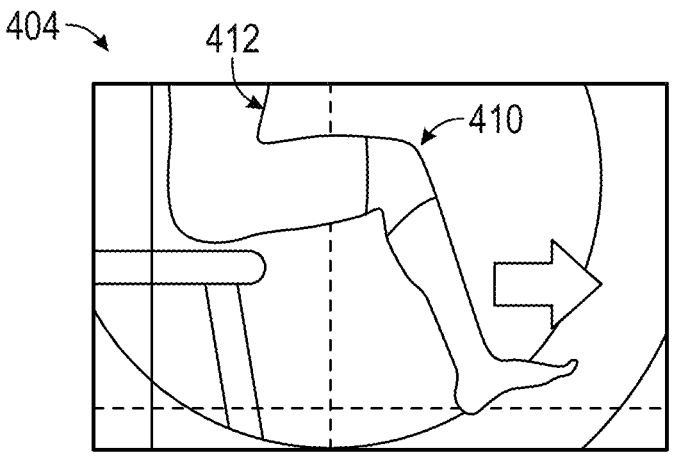

In some embodiments, the remote examination system 100 includes the master display 136. The master console 124 and/or the clinical portal 134 may comprise the master display 136. The master display 136 may be configured to display the treatment device 106 and/or one or more body parts of a patient. For example, the slave computing device 102 may be operatively coupled to an imaging device 116 (e.g., a camera or any other suitable audiovisual device) and/or other sensorial or perceptive (e.g., tactile, gustatory, haptic, pressure-sensing-based or electromagnetic (e.g., neurostimulation) communication devices. Any reference herein to any particular sensorial modality shall be understood to include and to disclose by implication a different one or more sensory modalities. The slave computing device 102 can transmit, via the network 104, real images and/or a real live-streaming video of the treatment device 106 and/or the patient, to the master display 136. The real images and/or real video may include angles of extension and/or bend of body parts of the patient, or any other suitable characteristics of the patient. The treatment device 106 may be operatively coupled to a medical device, such as a goniometer. The goniometer may detect angles of extension and/or bend of body parts of the patient and transmit the measured angles to the slave computing device 102 and/or the treatment device 106. The slave computing device 102 can transmit the measured angles to the master computing device 122, to the master display 136, or any other suitable device. The master display 136 can display the measured angles in numerical format, as an overlay image on the image of the treatment device 106 and/or the patient's one or more body parts, any other suitable format, or combination thereof. For example, as illustrated in FIG. 4A, body parts (e.g., a leg and a knee) are extended at a first angle. In FIG. 4B, the body parts are illustrated as being extended at a second angle. The master display 136 may be included in an electronic device that includes the one or more processing devices, memory devices, and/or network interface cards.

Depending on what result is desired, the master computing device 122 and/or a training engine 146 may be trained to output a guide map. The guide map may be overlaid on the augmented image 400. The guide map may include one or more indicators. To guide the master device 126, the indicators can be positioned over one or more sections 310 of the augmented image 400 of the treatment device 106. For example, the augmented image 402 may include a first indicator (e.g., dotted lines in the shape of a fingertip) positioned over a top portion of patient's knee and a second indicator positioned over a left side of the patient's knee. The first indicator is a guide for the healthcare provider to place the first finger 302 on the first indicator and the second finger 304 on the second indicator. The guide map may comprise a pressure gradient map. The pressure gradient map can include the current measured levels of force at the location of the indicator and/or a desired measured level of force at the location of the indicator. For example, the first indicator may comprise a first color, a first size, or any other suitable characteristic to indicate a first measured level of force. The second indicator may comprise a second color, a second size, or any other suitable characteristic to indicate a second measured level of force. When the master device 126 reaches the desired measured levels of force, an alert may be provided. The alert may be a visual, audio and/or another alert. For example, the alert may comprise the indicator changing colors when the measured level of force is provided. The guide map may include one or more configurations using characteristics of the injury, the patient, the treatment plan, the recovery results, the examination results, any other suitable factors, or any combinations thereof. One or more configurations may be displayed during the remote examination portion of a telemedicine session.

The master computing device 122 and/or the training engine 146 may include one or more thresholds, such as pressure thresholds. The one or more pressure thresholds may be based on characteristics of the injury, the patient, the treatment plan, the recovery results, the examination results, the pain level, any other suitable factors, or any combinations thereof. For example, one pressure threshold pertaining to the pain level of the patient may include a pressure threshold level for the slave pressure system 110 not to inflate a particular section 210 more than a first measured level of force. As the pain level of the patient decreases, the pressure threshold may change such that a second measured level of force may be applied to that particular section 210. In this case, the patient's decreased pain level may, for more optimal examination results (e.g., the second measured level of force is greater than the first measured level of force), allow for the healthcare provider to increase the measured amount of pressure applied to the patient's body part. Similarly, the master computing device 122 and/or the training engine 146 may be configured to adjust any predetermined manipulation instructions. In this way, the manipulation instructions can be adapted to the specific patient.

In other embodiments, the master display 136 can display an augmented image (e.g., exemplary augmented images 400 illustrated in FIG. 4), an augmented live-streaming video, a holographic image, any other suitable transmission, or any combination thereof of the treatment device 106 and/or one or more body parts of the patient. For example, the master display 136 may project an augmented image 402 representing the treatment device 106 (e.g., a knee brace 202). The augmented image 402 can include a representation 410 of the knee brace 202. The augmented image 402 can include a representation 412 of one or more body parts of a patient. Using the master device 126, the healthcare provider can place a hand on the image and manipulate the image (e.g., apply pressure virtually to one or more sections of the patient's knee via the treatment device 106. The one or more processing devices may cause a network interface card to transmit the data to the master computing device 122 and the master computing device 122 may use the data representing pressure, temperature, and patterns of movement to track measurements taken by the patient's recovery over certain time periods (e.g., days, weeks, etc.). In FIG. 4, the augmented images 400 are two dimensional, but the augmented images 400 may be transmitted as three-dimensional images or as any other suitable image dimensionality.

The master display 136 can be configured to display information obtained from a wristband. The information may include motion measurements of the treatment device 106 in the X, Y, and Z directions, altitude measurements, orientation measurements, rotation measurements, any other suitable measurements, or any combinations thereof. The wristband may be operatively coupled to an accelerometer, an altimeter, and/or a gyroscope. The accelerometer, the altimeter, and/or the gyroscope may be operatively coupled to a processing device in the wristband and may transmit data to the one or more processing devices. The one or more processing devices may cause a network interface card to transmit the data to the master computing device 122 and the master computing device 122 may use the data representing acceleration, frequency, duration, intensity, and patterns of movement to track measurements taken by the patient over certain time periods (e.g., days, weeks, etc.). Executing the clinical portal 134, the master computing device 122 may transmit the measurements to the master display 136. Additionally, in some embodiments, the processing device of the wristband may determine the measurements taken and transmit the measurements to the slave computing device 102. The measurements may be displayed on the patient portal 114. In some embodiments, the wristband may measure heartrate by using photoplethysmography (PPG), which detects an amount of red light or green light on the skin of the wrist. For example, blood may absorb green light so when the heart beats, the blood volume flow may absorb more green light, thereby enabling heartrate detection. In some embodiments, the wristband may be configured to detect temperature of the patient. The heartrate, temperature, any other suitable measurement, or any combination thereof may be sent to the master computing device 122.

Figure 4C:
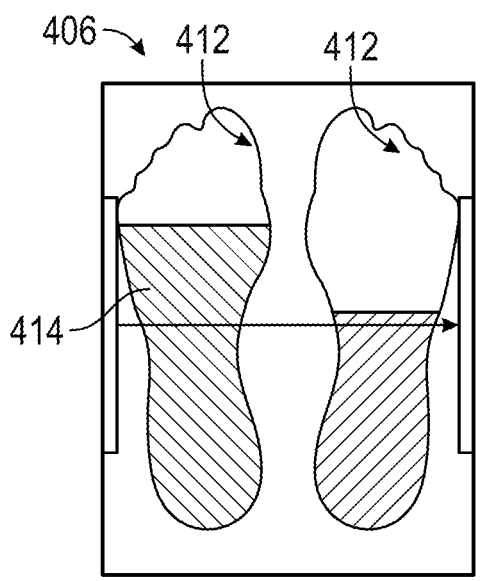
Figure 4D:
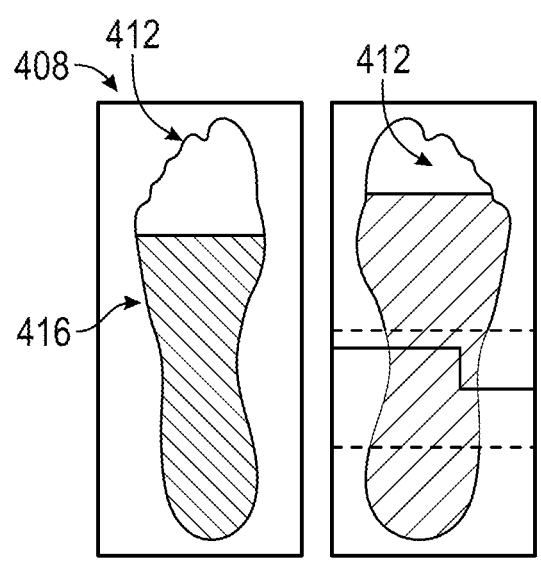

The master computing device 122 may present the measurements (e.g., pressure or temperature) of the body part of the patient taken by the treatment device 106 and/or the heartrate of the patient via a graphical indicator (e.g., a graphical element) on the clinical portal 134. The measurements may be presented as a gradient map, such as a pressure gradient map or a temperature gradient map. The map may be overlaid over the image of the treatment device 106 and/or the image of the patient's body part. For example, FIG. 4C illustrates an exemplary augmented image 406 displaying a pressure gradient 414 over the image of the patient's body parts 412 (e.g., feet). FIG. 4D illustrates an exemplary augmented image 408 displaying a temperature gradient 416 over the image of the patient's body parts 412 (e.g., feet).

Referring back to FIG. 1, the remote examination system 100 may include a cloud-based computing system 142. In some embodiments, the cloud-based computing system 142 may include one or more servers 144 that form a distributed computing architecture. Each of the servers 144 may include one or more processing devices, memory devices, data storage devices, and/or network interface cards. The servers 144 may be in communication with one another via any suitable communication protocol. The servers 144 may store profiles for each of the users (e.g., patients) configured to use the treatment device 106. The profiles may include information about the users such as a treatment plan, the affected body part, any procedure the user had had performed on the affected body part, health, age, race, measured data from the imaging device 116, slave sensor data, measured data from the wristband, measured data from the goniometer, user input received at the patient portal 114 during the telemedicine session, a level of discomfort the user experienced before and after the remote examination, before and after remote examination images of the affected body part(s), and so forth.

In some embodiments, the cloud-based computing system 142 may include a training engine 146 capable of generating one or more machine learning models 148. The machine learning models 148 may be trained to generate treatment plans, procedures for the remote examination, or any other suitable medical procedure for the patient in response to receiving various inputs (e.g., a procedure via a remote examination performed on the patient, an affected body part the procedure was performed on, other health characteristics (age, race, fitness level, etc.)). The one or more machine learning models 148 may be generated by the training engine 146 and may be implemented in computer instructions executable by one or more processing devices of the training engine 146 and/or the servers 144.

To generate the one or more machine learning models 148, the training engine 146 may train the one or more machine learning models 148. The training engine 146 may use a base data set of patient characteristics, results of remote examination(s), treatment plans followed by the patient, and results of the treatment plan followed by the patients. The results may include information indicating whether the remote examination led to an identification of the affected body part and whether the identification led to a partial recovery of the affected body part or lack of recovery of the affected body part. The results may include information indicating the measured levels of force applied to the one or more sections of the treatment device 106.

The training engine 146 may be a rackmount server, a router computer, a personal computer, an Internet of Things (IoT) device, a portable digital assistant, a smartphone, a laptop computer, a tablet computer, a camera, a video camera, a netbook, a desktop computer, a media center, any other desired computing device, or any combination of the above. The training engine 146 may be cloud-based or a real-time software platform, and it may include privacy software or protocols, and/or security software or protocols.

The one or more machine learning models 148 may also be trained to translate characteristics of patients received in real-time (e.g., from an electronic medical records (EMR) system, from the slave sensor data, etc.). The one or more machine learning models 148 may refer to model artifacts that are created by the training engine 146 using training data that includes training inputs and corresponding target outputs. The training engine 146 may find patterns in the training data that map the training input to the target output, and generate the machine learning models 148 that capture these patterns. Although depicted separately from the slave computing device 102, in some embodiments, the training engine 146 and/or the machine learning models 148 may reside on the slave computing device 102 and/or the master computing device 122.

Different machine learning models 148 may be trained to recommend different optimal examination procedures for different desired results. For example, one machine learning model may be trained to recommend optimal pressure maps for most effective examination of a patient, while another machine learning model may be trained to recommend optimal pressure maps using the current pain level and/or pain level tolerance of a patient.

The machine learning models 148 may include one or more of a neural network, such as an image classifier, recurrent neural network, convolutional network, generative adversarial network, a fully connected neural network, or some combination thereof, for example. In some embodiments, the machine learning models 148 may be composed of a single level of linear or non-linear operations or may include multiple levels of non-linear operations. For example, the machine learning model may include numerous layers and/or hidden layers that perform calculations (e.g., dot products) using various neurons.

FIGS. 1-4 are not intended to be limiting: the remote examination system 100 may include more or fewer components than those illustrated in FIGS. 1-4.

Figure 5:
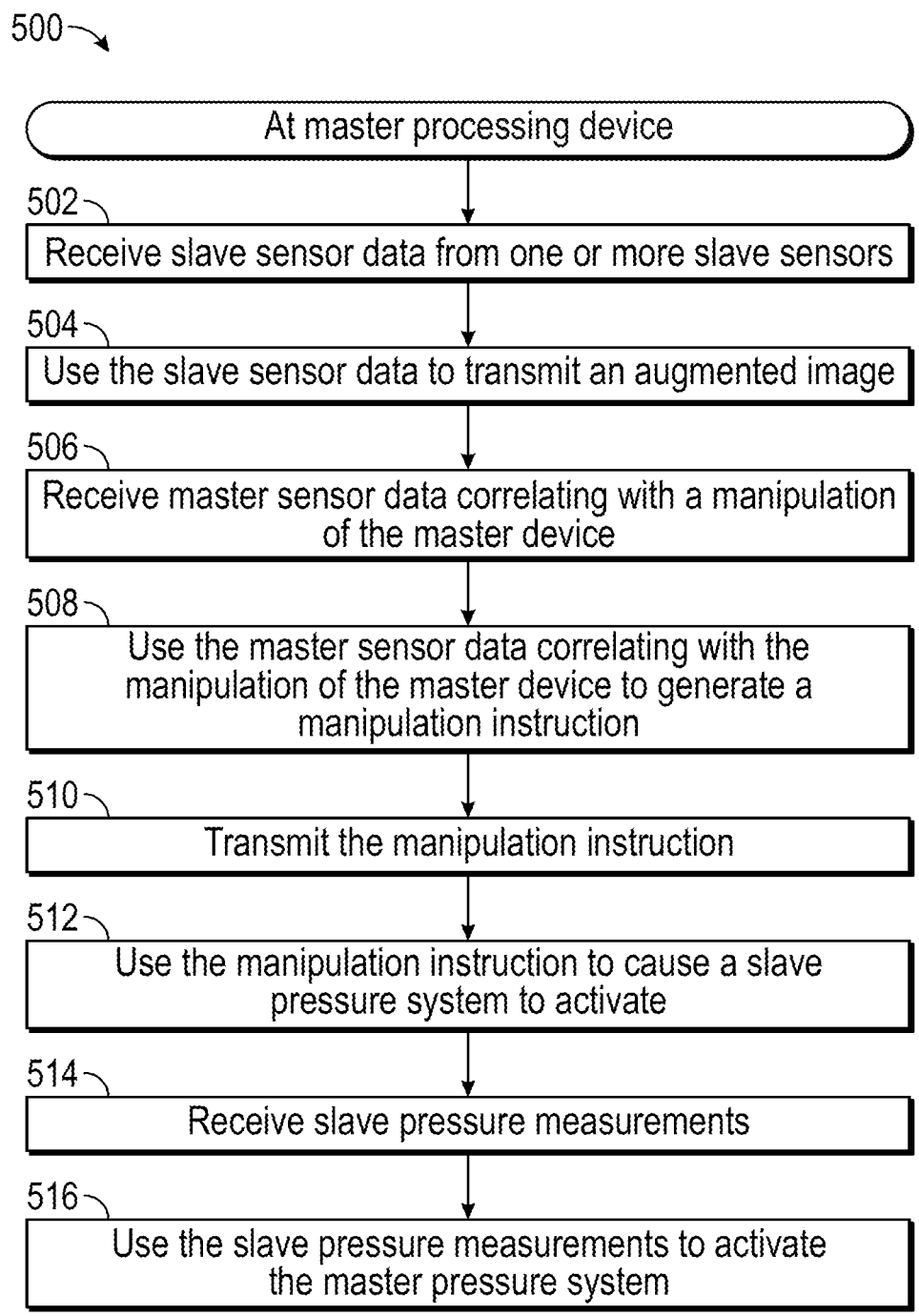
FIG. 5 generally illustrates an example method of operating a remote examination system according to certain aspects of this disclosure.

FIG. 5 illustrates a computer-implemented method 500 for remote examination. The method 500 may be performed by the remote examination system 100, such as at a master processing device. The processing device is described in more detail in FIG. 6. The steps of the method 500 may be stored in a non-transient computer-readable storage medium. Any or all of the steps of method 500 may be implemented during a telemedicine session or at any other desired time.

At step 502, the method 500 includes the master processing device receiving slave sensor data from one or more slave sensors 108. The master processing device may receive, via the network 104, the slave sensor data from a slave processing device.

At step 504, the master processing device can transmit an augmented image 400. The augmented image 400 may be based on the slave sensor data.

At step 506, the master processing device receives master sensor data correlating with a manipulation of the master device 126. For example, the master sensor data may include a measured level of force that the user, such as a healthcare provider, applied to the master device 126.

At step 508, the master processing device can generate a manipulation instruction. The manipulation instruction is based on the master sensor data correlating with the manipulation of the master device 126.

At step 510, the master processing device transmits the manipulation instruction. The master processing device may transmit, via the network 104, the manipulation instruction to the slave computing device 102.

At step 512, the master processing device causes the slave pressure system to activate. Using the manipulation instruction, the slave computing device 102 can cause the treatment device 106 to activate the slave pressure system 110. For example, responsive to the manipulation instruction (e.g., to increase and/or decrease one or more measured levels of force in one or more sections of the treatment device), the slave pressure system 110 can cause the slave controller 118 to activate the slave motor 112 to inflate and/or deflate the one or more sections 210 to one or more measured levels of force.

At step 514, the master processing device receives slave force measurements. The slave force measurements can include one or more measurements correlating with one or more measured levels of force that the patient's body is applying to the treatment device 106.

At step 516, the master processing device uses the pressure slave measurements to activate the master pressure system 130. For example, the master pressure system 130 can cause the master device 126 to inflate and/or deflate one or more sections 310 of the master device 126 such that the measured levels of force of the one or more sections 310 directly correlate with the one or more measured levels of force that the patient's body is applying to the one or more sections 210 of the treatment device 106.

Figure 6:
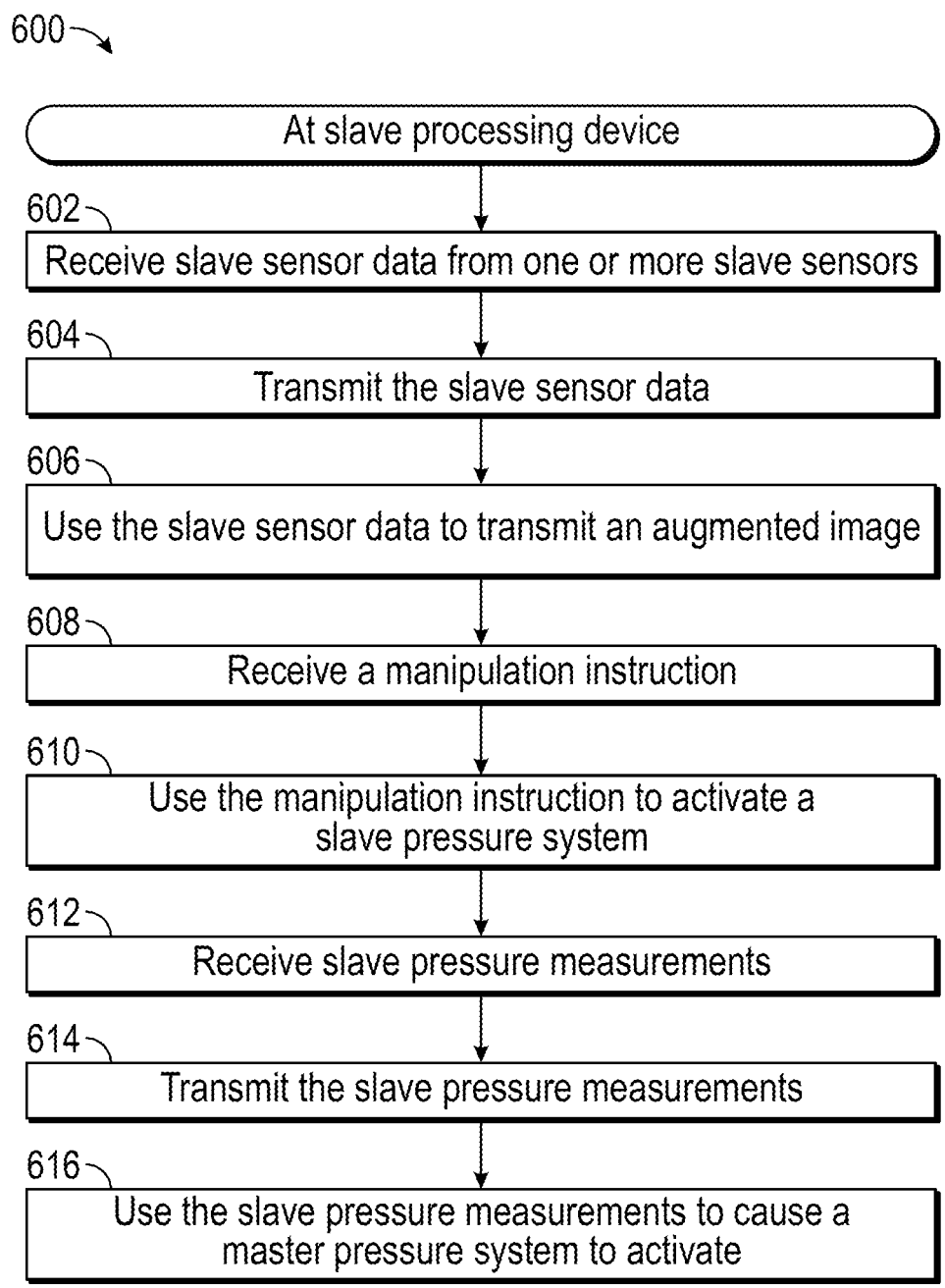
FIG. 6 generally illustrates an example method of operating a remote examination system according to certain aspects of this disclosure.

FIG. 6 illustrates a computer-implemented method 600 for remote examination. The method 600 may be performed by the remote examination system 100, such as at a slave processing device. The processing device is described in more detail in FIG. 6. The steps of the method 600 may be stored in a non-transient computer-readable storage medium. Any or all of the steps of method 600 may be implemented during a telemedicine session or at any other desired time.

At step 602, the method 600 includes the slave processing device receiving slave sensor data from one or more slave sensors 108. The one or more slave sensors 108 may include one or more measured levels of force that the patient's body is applying to the treatment device 106.

At step 604, the slave processing device transmits the slave sensor data. The slave processing device may transmit, via the network 104, the slave sensor data to the master computing device 122.

At step 606, the slave processing device may transmit an augmented image 400. The augmented image 400 is based on the slave sensor data. For example, the augmented image 400 may include a representation of the treatment device 106, one or more body parts of the patient, measured levels of force, measured levels of temperature, any other suitable information, or combination thereof.

At step 608, the slave processing device receives a manipulation instruction. The manipulation instruction can be generated based on the master sensor data.

At step 610, using the manipulation instruction, the slave processing device activates the slave pressure system 110. For example, the manipulation instruction may cause the slave pressure system 110 to inflate and/or deflate one or more sections 210 of the treatment device 106 to correlate with one or more levels of force applied to one or more sections 310 of the master device 126.

At step 612, the slave processing device receives slave force measurements. The slave force measurements can include one or more measured levels of force exerted by the patient's body to the treatment device 106.

At step 614, the slave processing device transmits the slave force measurements, such as to the master processing device.

At step 616, using the slave force measurements, the slave processing device causes a master pressure system 130 to activate. For example, the master pressure system 130 can cause the master device 126 to inflate and/or deflate one or more sections 310 of the master device 126 such that the measured levels of force of the one or more sections 310 correlate with the one or more measured levels of force that the patient's body is applying to the one or more sections 210 of the treatment device 106.

FIGS. 5-6 are not intended to be limiting: the methods 500, 600 can include more or fewer steps and/or processes than those illustrated in FIGS. 5-6. Further, the order of the steps of the methods 500, 600 is not intended to be limiting; the steps can be arranged in any suitable order. Any or all of the steps of methods 500, 600 may be implemented during a telemedicine session or at any other desired time.

Figure 7:
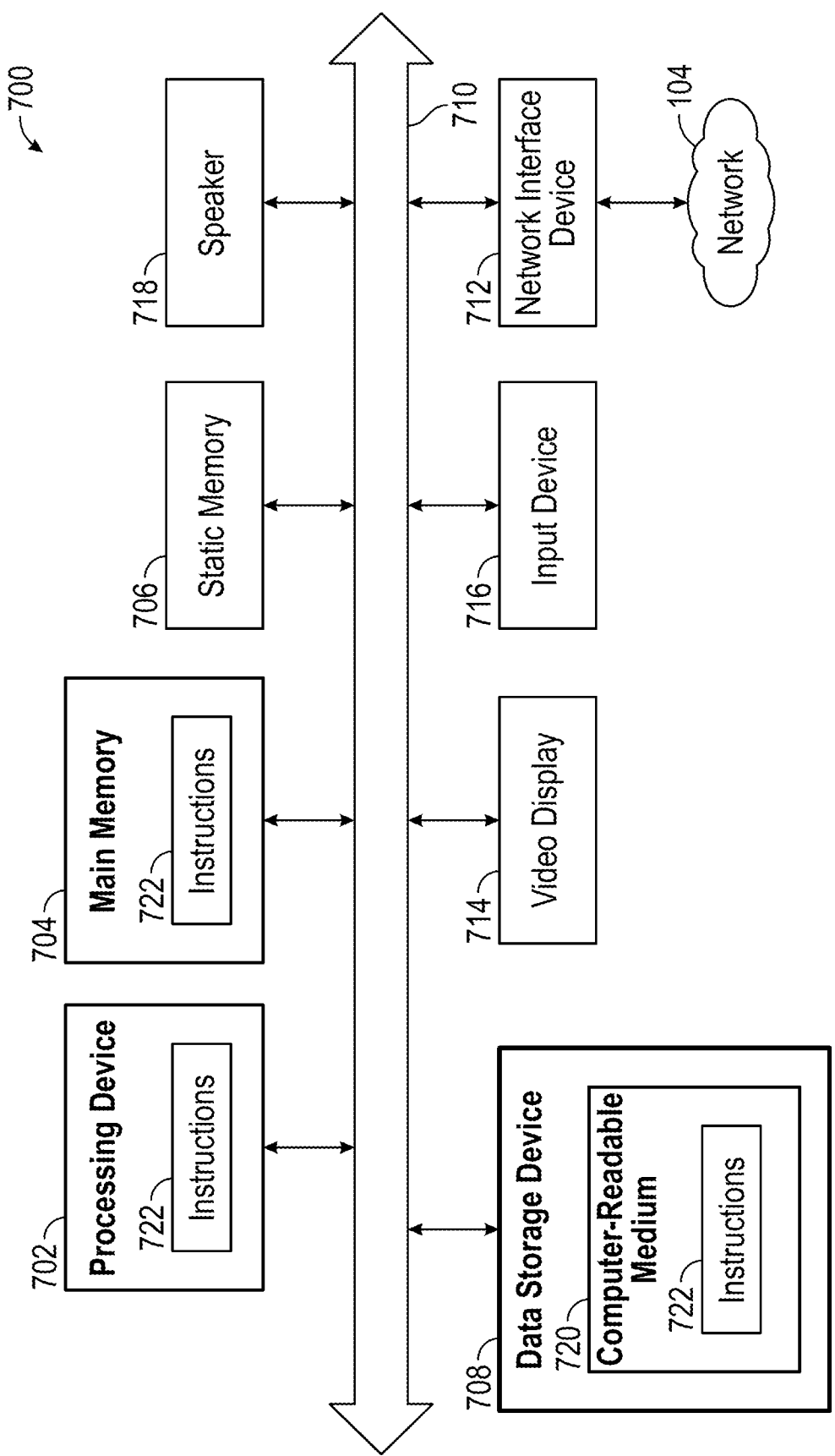
FIG. 7 generally illustrates an example computer system according to certain to certain aspects of this disclosure.

FIG. 7 illustrates, in accordance with one or more aspects of the present disclosure, an example computer system 700 which can perform any one or more of the methods described herein. The computer system 700 may correspond to the slave computing device 102 (e.g., a patient's computing device), the master computing device 122 (e.g., a healthcare provider's computing device), one or more servers of the cloud-based computing system 142, the training engine 146, the server 144, the slave pressure system 110, the master pressure system 130, the slave controller 118, the master controller 138, the imaging device 116, the master display 136, the treatment device 106, the master device 126, and/or the master console 124 of FIG. 1. The computer system 700 may be capable of executing the patient portal 114 and/or clinical portal 134 of FIG. 1. The computer system 700 may be connected (e.g., networked) to other computer systems in a LAN, an intranet, an extranet, or the Internet. The computer system 700 may operate in the capacity of a server in a client-server network environment. The computer system may be a personal computer (PC), a tablet computer, a motor controller, a goniometer, a wearable (e.g., wristband), a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 700 includes a processing device 702 (e.g., the slave processing device, the master processing device), a main memory 704 (e.g., read-only memory (ROM), flash memory, dynamic random access memory (DRAM) such as synchronous DRAM (SDRAM)), a static memory 706 (e.g., flash memory, static random access memory (SRAM)), and a data storage device 708, which communicate with each other via a bus 710.

The processing device 702 represents one or more general-purpose processing devices such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 702 may also be one or more special-purpose processing devices such as an application specific integrated circuit (ASIC), a field programmable gate array (FPGA), a digital signal processor (DSP), network processor, or the like. The processing device 702 is configured to execute instructions for performing any of the operations and steps discussed herein.

The computer system 700 may further include a network interface device 712. The computer system 700 also may include a video display 714 (e.g., a liquid crystal display (LCD), a light-emitting diode (LED), an organic light-emitting diode (OLED or Organic LED), or a cathode ray tube (CRT)). The video display 714 can represent the master display 136 or any other suitable display. The computer system 700 may include one or more input devices 716 (e.g., a keyboard, a mouse, the goniometer, the wristband, the imaging device 116, or any other suitable input). The computer system 700 may include one or more output devices (e.g., a speaker 718). In one illustrative example, the video display 714, the input device(s) 716, and/or the speaker 718 may be combined into a single component or device (e.g., an LCD touch screen).

The data storage device 708 may include a computer-readable medium 720 on which the instructions 722 (e.g., implementing the control system, the patient portal 114, the clinical portal 134, and/or any functions performed by any device and/or component depicted in the FIGS. and described herein) embodying any one or more of the methodologies or functions described herein are stored. The instructions 722 may also reside, completely or at least partially, within the main memory 704 and/or within the processing device 702 during execution thereof by the computer system 700. As such, the main memory 704 and the processing device 702 also constitute computer-readable media. The instructions 722 may further be transmitted or received over a network via the network interface device 712.

While the computer-readable storage medium 720 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In one exemplary embodiment, the computer system 700 includes the input device 716 (e.g., the master console 124 comprising the master device 126) and the control system comprising the processing devices 702 (e.g., the master processing device) operatively coupled to the input device 716 and the treatment device 106. The system 700 may comprise one or more memory devices (e.g., main memory 704, data storage device 708, etc.) operatively coupled to the processing device 702. The one or more memory devices can be configured to store instructions 722. The processing device 702 can be configured to execute the instructions 722 to receive the slave sensor data from the one or more slave sensors 108, to use a manipulation of the master device 126 to generate a manipulation instruction, to transmit the manipulation instruction, and to use the manipulation instruction to cause the slave pressure system 110 to activate. The instructions can be executed in real-time or near real-time.

The processing device 702 can be further configured to use the slave sensor data to transmit an augmented image 400 to the video display (e.g., the master display 136). The healthcare provider may view the augmented image 400 and/or virtually touch the augmented image using the video display 714. In other words, the augmented image 400 may comprise a representation of the treatment device 106 and one or more body parts of the patient. The representation may be displayed in 2D, 3D, or any other suitable dimension. As the healthcare provider conducts the remote examination during a telemedicine session, the augmented image 400 may change to reflect the manipulations of the treatment device 106 and/or of any movement of the patient's one or more body parts.

The augmented image 400 can comprise one or more pressure indicators, temperature indicators, any other suitable indicator, or combination thereof. Each pressure indicator can represent a measured level of force (i.e., based on the slave force measurements). Each temperature indicator can represent a measured level of temperature (i.e., based on the slave temperature measurements). For example, the pressure indicators and/or the temperature indicators may be different colors, each color correlating with one of the measured levels of force and temperature, respectively. The indicators may be displayed as a map. The map may be a gradient map displaying the pressure indicators and/or temperature indicators. The map may be overlaid over the augmented image. The map may be transmitted to the clinical portal, the master display, the patient portal, any other suitable display, or combination thereof The processing device 702 can be further configured to use the slave sensor data (e.g., the slave force measurements) to provide a corresponding level of measured force to the master device 126. In other words, while using the master device 126, the healthcare provider can essentially feel the measured levels of force exerted by the patient's one or more body parts during the remote examination.

As the healthcare provider is virtually examining the patient, the processing device 702 can use the master sensor data to generate and transmit the manipulation instruction (e.g., a measured level of force) to manipulate the treatment device 106. In other words, as the healthcare provider applies more force pressure) to the master device 126, the master sensors 128 can detect the measured level of force and instruct the treatment device 106 to apply a correlated measured level of force. In some embodiments, the measured level of force can be based on a proximity of the master device 126 to the representation. In other words, as the healthcare provider manipulates the master device 126 closer to the representation and/or within the representation of the treatment device 126 and/or the patient's one or more body parts, the master sensors 128 can detect that the measured force has increased. In some embodiments, the input device 716 can comprise a pressure gradient. Using the pressure gradient, the processing device 702 can be configured to cause the slave pressure system 110 to apply one or more measured levels of force to one or more sections 210 of the treatment device 106.

In another exemplary embodiment, the computer system 700 may include the input device 716 (e.g., the treatment device 106) and the control system comprising the processing device 702 (e.g., the slave processing device) operatively coupled to the input device 716 and the master device 126. The system 700 may comprise one or more memory devices (e.g., main memory 704, data storage device 708, etc.) operatively coupled to the processing device 702. The one or more memory devices can be configured to store instructions 722. The processing device 702 can be configured to execute the instructions 722 to receive the slave sensor data from the one or more slave sensors 108, to transmit the slave sensor data, to receive the manipulation instruction, and to use the manipulation instruction to activate the slave pressure system 110. The instructions can be executed in real-time or near real-time.

In yet another embodiment, the computer system 700 may include one or more input devices 716 (e.g., the master console 124 comprising the master device 126, the treatment device 106, etc.) and the control system comprising one or more processing devices 702 (e.g., the master processing device, the slave processing device) operatively coupled to the input devices 716. For example, the master processing device may be operatively coupled to the master console 124 and the slave processing device may be operatively coupled to the treatment device 106. The system 700 may comprise one or more memory devices (e.g., master memory coupled to the master processing device, slave memory coupled to the slave processing device, etc.) operatively coupled to the one or more processing devices 702. The one or more memory devices can be configured to store instructions 722 (e.g., master instructions, slave instructions, etc.). The one or more processing devices 702 (e.g., the master processing device) can be configured to execute the master instructions 722 to receive the slave sensor data from the slave processing device, use a manipulation of the master device 126 to generate a manipulation instruction, and transmit the manipulation instruction to the slave processing device. The one or more processing devices 702 (e.g., the slave processing device) can be configured to execute the slave instructions 722 to receive the slave sensor data from the one or more slave sensors, to transmit the slave sensor data to the master processing device, to receive the manipulation instruction from the master processing device, and to use the manipulation instruction to activate the slave pressure system. The instructions can be executed in real-time or near real-time.

FIG. 7 is not intended to be limiting: the system 700 may include more or fewer components than those illustrated in FIG. 7.

Any of the systems and methods described in this disclosure may be used in connection with rehabilitation. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the throracic cavity. Prehabilitation can improve a patient's speed of recovery, measure of quality of life, level of pain, etc. in all of the foregoing procedures. In one embodiment of prehabilitation, a pre-surgical procedure or a pre-non-surgical-treatment may include one or more sets of exercises for a patient to perform prior to such procedure or treatment. The patient may prepare an area of his or her body for the surgical procedure by performing the one or more sets of exercises, thereby strengthening muscle groups, improving existing and/or establishing new muscle memory, enhancing mobility, improving blood flow, and/or the like.

In some embodiments, the systems and methods described herein may use artificial intelligence and/or machine learning to generate a prehabilitation treatment plan for a user. Additionally, or alternatively, the systems and methods described herein may use artificial intelligence and/or machine learning to recommend an optimal exercise machine configuration for a user. For example, a data model may be trained on historical data such that the data model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the patient, a recommended health professional specialist to contact, and/or the like.

Consistent with the above disclosure, the examples of systems and methods enumerated in the following clauses are specifically contemplated and are intended as a non-limiting set of examples.

Clause 1. A computer-implemented system, comprising:
a treatment device comprising one or more slave sensors and a slave pressure system, the treatment device configured to be manipulated while a patient performs a treatment plan;
a master console comprising a master device;
a user interface comprising an output device configured to present telemedicine information associated with a telemedicine session; and
a control system comprising one or more processing devices operatively coupled to the master console and the treatment device, wherein the one or more processing devices are configured to:
receive slave sensor data from the one or more slave sensors;
use a manipulation of the master device to generate a manipulation instruction;
transmit the manipulation instruction; and
during the telemedicine session, use the manipulation instruction to cause the slave pressure system to activate.

Clause 2. The computer-implemented system of any clause herein, wherein the slave sensor data comprises slave force measurements;
wherein the master device comprises a master pressure system; and
wherein, using the slave force measurements, the one or more processing devices are further configured to activate the master pressure system.

Clause 3. The computer-implemented system of any clause herein, wherein the master device comprises a pressure gradient; and
wherein, using the pressure gradient, the one or more processing devices are configured to cause the slave pressure system to apply one or more measured levels of force to one or more sections of the treatment device.

Clause 4. The computer-implemented system of any clause herein, wherein the treatment device comprises at least one of a physical therapy device, a brace, a mat, and a wrap.

Clause 5. A system for a remote examination of a patient, comprising:
a master console comprising a master device;
a treatment device comprising one or more slave sensors and a slave pressure system; and
a control system comprising one or more processing devices operatively coupled to the master console and the treatment device, wherein the one or more processing devices are configured to:
receive slave sensor data from the one or more slave sensors;
use a manipulation of the master device to generate a manipulation instruction;
transmit the manipulation instruction; and
use the manipulation instruction to cause the slave pressure system to activate.

Clause 6. The system of any clause herein, wherein the master device comprises master sensors for detecting master sensor data correlating with the manipulation; and
wherein the manipulation instruction is based on the master sensor data.

Clause 7. The system of any clause herein, wherein the slave sensor data comprises slave force measurements;

wherein the master device comprises a master pressure system; and wherein, using the slave force measurements, the one or more processing devices are further configured to activate the master pressure system.

Clause 8. The system of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 9. The system of any clause herein, wherein the one or more processing devices are further configured to:

use the slave sensor data to transmit an augmented image to a master display.

Clause 10. The system of any clause herein, wherein the slave sensor data comprises slave force measurements;

wherein the augmented image comprises one or more pressure indicators; and wherein the one or more pressure indicators are based on the slave force measurements.

Clause 11. The system of any clause herein, wherein the slave sensor data comprises slave temperature measurements;

wherein the augmented image comprises one or more temperature indicators; and wherein the one or more temperature indicators are based on the slave temperature measurements.

Clause 12. The system of any clause herein, wherein the master device comprises a pressure gradient; and wherein, using the pressure gradient, the one or more processing devices are configured to cause the slave pressure system to apply one or more measured levels of force to one or more sections of the treatment device.

Clause 13. The system of any clause herein, wherein the augmented image comprises a representation of at least one of the treatment device and a body part of the patient, and wherein the representation is in 2D or 3D.

Clause 14. The system of any clause herein, wherein the manipulation instruction comprises a measured level of force; and wherein the measured level of force is based on a proximity of the master device to the representation.

Clause 15. The system of any clause herein, wherein the one or more processing devices are further configured to:

transmit the manipulation instruction in real-time or near real-time; and cause the slave pressure system to activate in real-time or near real-time.

Clause 16. The system of any clause herein, wherein the master device comprises at least one of a glove device, a joystick, and a model of the treatment device.

Clause 17. The system of any clause herein, wherein the treatment device comprises at least one of a physical therapy device, a brace, a mat, and a wrap.

Clause 18. The system of any clause herein, further comprising one or more memory devices operatively coupled to the one or more processing devices, wherein the one or more memory devices stores instructions, and wherein the one or more processing devices are configured to execute the instructions.

Clause 19. A method for operating a system for remote examination of a patient, comprising:

receiving slave sensor data from one or more slave sensors;

based on a manipulation of a master device, generating a manipulation instruction;

transmitting the manipulation instruction; and based on the manipulation instruction, causing a slave pressure system to activate.

Clause 20. The method of any clause herein, wherein the master device comprises master sensors for detecting master sensor data correlating with the manipulation; and wherein the manipulation instruction is based on the master sensor data.

Clause 21. The method of any clause herein, wherein the slave sensor data comprises slave force measurements;

wherein the master device comprises a master pressure system; and wherein, based on the slave force measurements, activating the master pressure system.

Clause 22. The method of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 23. The method of any clause herein, further comprising:

use the slave sensor data to transmitting an augmented image.

Clause 24. The method of any clause herein, wherein the slave sensor data comprises slave force measurements;

wherein the augmented image comprises one or more pressure indicators; and wherein the one or more pressure indicators are based on the slave force measurements.

Clause 25. The method of any clause herein, wherein the slave sensor data comprises slave temperature measurements;

wherein the augmented image comprises one or more temperature indicators; and wherein the one or more temperature indicators are based on the slave temperature measurements.

Clause 26. The method of any clause herein, wherein the master device comprises a pressure gradient; and wherein, using the pressure gradient, causing the slave pressure system to apply one or more measured levels of force to one or more sections of the treatment device.

Clause 27. The method of any clause herein, wherein the augmented image comprises a representation of at least one of the treatment device and a body part of the patient, and wherein the representation is in 2D or 3D.

Clause 28. The method of any clause herein, wherein the manipulation instruction comprises a measured level of force; and wherein the measured level of force is based on a proximity of the master device to the representation.

Clause 29. The method of any clause herein, further comprising:

transmitting the manipulation instruction in real-time or near real-time; and causing the slave pressure system to activate in real-time or near real-time.

Clause 30. The method of any clause herein, wherein the master device comprises at least one of a glove device, a joystick, and a model of the treatment device.

Clause 31. The method of any clause herein, wherein the treatment device comprises at least one of a physical therapy device, a brace, a mat, and a wrap.

Clause 32. A tangible, non-transitory computer-readable storage medium storing instructions that, when executed, cause a processing device to:
 receive slave sensor data from one or more slave sensors;
 based on a manipulation of a master device, generate a manipulation instruction;
 transmit the manipulation instruction; and
 use the manipulation instruction to cause a slave pressure system to activate.

Clause 33. The tangible, non-transitory computer-readable storage medium of any clause herein, wherein the master device comprises master sensors for detecting master sensor data correlating with the manipulation; and
 wherein the manipulation instruction is based on the master sensor data.

Clause 34. The tangible, non-transitory computer-readable storage medium of any clause herein, wherein the slave sensor data comprises slave force measurements;
 wherein the master device comprises a master pressure system; and
 wherein, based on the slave force measurements, activate the master pressure system.

Clause 35. The tangible, non-transitory computer-readable storage medium of any clause herein, further comprising:
 a second master device comprising a second master pressure system;
 wherein the slave sensor data comprises slave force measurements; and
 wherein, using the slave force measurements, the one or more processing devices are further configured to activate the second master pressure system.

Clause 36. The tangible, non-transitory computer-readable storage medium of any clause herein, wherein the instructions further cause the processing device to:
 use the slave sensor data to transmit an augmented image.

Clause 37. The tangible, non-transitory computer-readable storage medium of any clause herein, wherein the slave sensor data comprises slave force measurements;
 wherein the augmented image comprises one or more pressure indicators; and
 wherein the one or more pressure indicators are based on the slave force measurements.

Clause 38. The tangible, non-transitory computer-readable storage medium of any clause herein, wherein the slave sensor data comprises slave temperature measurements;
 wherein the augmented image comprises one or more temperature indicators; and
 wherein the one or more temperature indicators are based on the slave temperature measurements.

Clause 39. The tangible, non-transitory computer-readable storage medium of any clause herein, wherein the master device comprises a pressure gradient; and
 wherein, using the pressure gradient, cause the slave pressure system to apply one or more measured levels of force to one or more sections of the treatment device.

Clause 40. The tangible, non-transitory computer-readable storage medium of any clause herein, wherein the augmented image comprises a representation of at least one of the treatment device and a body part of the patient, and wherein the representation is in 2D or 3D.

Clause 41. The tangible, non-transitory computer-readable storage medium of any clause herein, wherein the manipulation instruction comprises a measured level of force; and
 wherein the measured level of force is based on a proximity of the master device to the representation.

Clause 42. The tangible, non-transitory computer-readable storage medium of any clause herein, wherein the instructions further cause the processing device to:
 transmit the manipulation instruction in real-time or near real-time; and
 cause the slave pressure system to activate in real-time or near real-time.

Clause 43. The tangible, non-transitory computer-readable storage medium of any clause herein, wherein the master device comprises at least one of a glove device, a joystick, and a model of the treatment device.

Clause 44. The tangible, non-transitory computer-readable storage medium of any clause herein, wherein the treatment device comprises at least one of a physical therapy device, a brace, a mat, and a wrap.

Clause 45. A system for a remote examination of a patient, comprising:
 a master console comprising a master device;
 a treatment device comprising one or more slave sensors and a slave pressure system; and
 a control system comprising one or more processing devices operatively coupled to the master console and the treatment device, wherein the one or more processing devices are configured to:
  receive slave sensor data from the one or more slave sensors;
  transmit the slave sensor data;
  receive a manipulation instruction; and
  use the manipulation instruction to activate the slave pressure system.

Clause 46. The system of any clause herein, wherein the manipulation instruction is based on a manipulation of the master device.

Clause 47. The system of any clause herein, wherein the master device comprises master sensors for detecting master sensor data correlating with the manipulation; and
 wherein the manipulation instruction is based on the master sensor data.

Clause 48. The system of any clause herein, further comprising:
 a second master device comprising a second master pressure system;
 wherein the slave sensor data comprises slave force measurements; and
 wherein, using the slave force measurements, the one or more processing devices are further configured to activate the second master pressure system.

Clause 49. The system of any clause herein, wherein the one or more processing devices are further configured to:
 use the slave sensor data to transmit an augmented image to the master console.

Clause 50. The system of any clause herein, wherein the slave sensor data comprises slave force measurements;
 wherein the master device comprises a master pressure system; and
 wherein, using the slave force measurements, the one or more processing devices are further configured to cause the master pressure system to activate.

Clause 51. The system of any clause herein, wherein the slave sensor data comprises slave force measurements;

wherein the augmented image comprises one or more pressure indicators; and wherein the one or more pressure indicators are based on the slave force measurements.

Clause 52. The system of any clause herein, wherein the slave sensor data comprises slave temperature measurements;

wherein the augmented image comprises one or more temperature indicators; and wherein the one or more temperature indicators are based on the slave temperature measurements.

Clause 53. The system of any clause herein, wherein the master device comprises a pressure gradient; and wherein, using the pressure gradient, activating the slave pressure system comprises applying one or more measured levels of force to one or more sections of the treatment device.

Clause 54. The system of any clause herein, wherein the augmented image comprises a representation of at least one of the treatment device and a body part of the patient, and wherein the representation is in 2D or 3D.

Clause 55. The system of any clause herein, wherein the manipulation instruction comprises a measured level of force; and wherein the measured level of force is based on a proximity of the master device to the representation.

Clause 56. The system of any clause herein, wherein the one or more processing devices are further configured to:

receive the manipulation instruction in real-time or near real-time; and activate the slave pressure system in real-time or near real-time.

Clause 57. The system of any clause herein, wherein the master device comprises at least one of a glove device, a joystick, and a model of the treatment device.

Clause 58. The system of any clause herein, wherein the treatment device comprises at least one of a physical therapy device, a brace, a mat, and a wrap.

Clause 59. The system of any clause herein, further comprising one or more memory devices operatively coupled to the one or more processing devices, wherein the one or more memory devices stores instructions, and wherein the one or more processing devices are configured to execute the instructions.

Clause 60. A method for operating a system for remote examination of a patient, comprising:

receiving slave sensor data from one or more slave sensors;

transmitting the slave sensor data;

receiving a manipulation instruction; and based on the manipulation instruction, activating a slave pressure system.

Clause 61. The method of any clause herein, wherein the manipulation instruction is based on a manipulation of a master device.

Clause 62. The method of any clause herein, wherein the master device comprises master sensors for detecting master sensor data correlating with the manipulation; and wherein the manipulation instruction is based on the master sensor data.

Clause 63. The method of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 64. The method of any clause herein, further comprising:

use the slave sensor data to transmitting an augmented image to the master console.

Clause 65. The method of any clause herein, wherein the slave sensor data comprises slave force measurements;

wherein the master device comprises a master pressure system; and wherein, based on the slave force measurements, causing the master pressure system to activate.

Clause 66. The method of any clause herein, wherein the slave sensor data comprises slave force measurements;

wherein the augmented image comprises one or more pressure indicators; and wherein the one or more pressure indicators are based on the slave force measurements.

Clause 67. The method of any clause herein, wherein the slave sensor data comprises slave temperature measurements;

wherein the augmented image comprises one or more temperature indicators; and wherein the one or more temperature indicators are based on the slave temperature measurements.

Clause 68. The method of any clause herein, wherein the master device comprises a pressure gradient; and wherein, using the pressure gradient, activating the slave pressure system comprises applying one or more measured levels of force to one or more sections of the treatment device.

Clause 69. The method of any clause herein, wherein the augmented image comprises a representation of at least one of the treatment device and a body part of the patient, and wherein the representation is in 2D or 3D.

Clause 70. The method of any clause herein, wherein the manipulation instruction comprises a measured level of force; and wherein the measured level of force is based on a proximity of the master device to the representation.

Clause 71. The method of any clause herein, further comprising:

receiving the manipulation instruction in real-time or near real-time; and activating the slave pressure system in real-time or near real-time.

Clause 72. The method of any clause herein, wherein the master device comprises at least one of a glove device, a joystick, and a model of the treatment device.

Clause 73. The method of any clause herein, wherein the treatment device comprises at least one of a physical therapy device, a brace, a mat, and a wrap.

Clause 74. A tangible, non-transitory computer-readable storage medium storing instructions that, when executed, cause a processing device to:

receive slave sensor data from one or more slave sensors;

transmit the slave sensor data;

receive a manipulation instruction; and use the manipulation instruction to activate a slave pressure system.

Clause 75. The tangible, non-transitory computer-readable storage medium of any clause herein, wherein the manipulation instruction is based on a manipulation of a master device.

Clause 76. The tangible, non-transitory computer-readable storage medium of any clause herein, wherein the master device comprises master sensors for detecting master sensor data correlating with the manipulation; and wherein the manipulation instruction is based on the master sensor data.

Clause 77. The tangible, non-transitory computer-readable storage medium of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 78. The tangible, non-transitory computer-readable storage medium of any clause herein, wherein the instructions further cause the processing device to:

use the slave sensor data to transmit an augmented image to the master console.

Clause 79. The tangible, non-transitory computer-readable storage medium of any clause herein, wherein the slave sensor data comprises slave force measurements;

wherein the master device comprises a master pressure system; and wherein, based on the slave force measurements, cause the master pressure system to activate.

Clause 80. The tangible, non-transitory computer-readable storage medium of any clause herein, wherein the slave sensor data comprises slave force measurements;

wherein the augmented image comprises one or more pressure indicators; and wherein the one or more pressure indicators are based on the slave force measurements.

Clause 81. The method of any clause herein, wherein the slave sensor data comprises slave temperature measurements;

wherein the augmented image comprises one or more temperature indicators; and wherein the one or more temperature indicators are based on the slave temperature measurements.

Clause 82. The method of any clause herein, wherein the master device comprises a pressure gradient; and wherein, using the pressure gradient, activating the slave pressure system comprises applying one or more measured levels of force to one or more sections of the treatment device.

Clause 83. The method of any clause herein, wherein the augmented image comprises a representation of at least one of the treatment device and a body part of the patient, and wherein the representation is in 2D or 3D.

Clause 84. The tangible, non-transitory computer-readable storage medium of any clause herein, wherein the manipulation instruction comprises a measured level of force; and wherein the measured level of force is based on a proximity of the master device to the representation.

Clause 85. The tangible, non-transitory computer-readable storage medium of any clause herein, wherein the instructions further cause the processing device to:

receive the manipulation instruction in real-time or near real-time; and activate the slave pressure system in real-time or near real-time.

Clause 86. The tangible, non-transitory computer-readable storage medium of any clause herein, wherein the master device comprises at least one of a glove device, a joystick, and a model of the treatment device.

Clause 87. The tangible, non-transitory computer-readable storage medium of any clause herein, wherein the treatment device comprises at least one of a physical therapy device, a brace, a mat, and a wrap.

Clause 88. A system for a remote examination of a patient, comprising:

a master console comprising a master device;

a treatment device comprising one or more slave sensors and a slave pressure system; and a control system comprising a master processing device and a slave processing device, wherein the master processing device is operatively coupled to the master console and the slave processing device is operatively coupled to the treatment device;

wherein the master processing device is configured to:
receive slave sensor data from the slave processing device;
use a manipulation of the master device to generate a manipulation instruction; and
transmit the manipulation instruction to the slave processing device; and wherein the slave processing device is configured to:
receive the slave sensor data from the one or more slave sensors;
transmit the slave sensor data to the master processing device;
receive the manipulation instruction from the master processing device; and
use the manipulation instruction to activate the slave pressure system.

Clause 89. The system of any clause herein, wherein the master device comprises master sensors for detecting master sensor data correlating with the manipulation; and wherein the manipulation instruction is based on the master sensor data.

Clause 90. The system of any clause herein, wherein the slave sensor data comprises slave force measurements;

wherein the master device comprises a master pressure system; and wherein, using the slave force measurements, the master processing device is further configured to activate the master pressure system.

Clause 91. The system of any clause herein, further comprising:

a second master device comprising a second master pressure system;

wherein the slave sensor data comprises slave force measurements; and wherein, using the slave force measurements, the master processing device is further configured to activate the second master pressure system.

Clause 92. The system of any clause herein, wherein the master processing device is further configured to:

use the slave sensor data to transmit an augmented image to a master display.

Clause 93. The system of any clause herein, wherein the slave sensor data comprises slave force measurements;

wherein the augmented image comprises one or more pressure indicators; and wherein the one or more pressure indicators are based on the slave force measurements.

Clause 94. The system of any clause herein, wherein the slave sensor data comprises slave temperature measurements;

wherein the augmented image comprises one or more temperature indicators; and wherein the one or more temperature indicators are based on the slave temperature measurements.

Clause 91. The system of any clause herein, wherein the master device comprises a pressure gradient; and wherein, using the pressure gradient, activating the slave pressure system comprises applying one or more measured levels of force to one or more sections of the treatment device.

Clause 96. The system of any clause herein, wherein the augmented image comprises a representation of at least one of the treatment device and a body part of the patient, and wherein the representation is in 2D or 3D.

Clause 97. The system of any clause herein, wherein the manipulation instruction comprises a measured level of force; and wherein the measured level of force is based on a proximity of the master device to the representation.

Clause 98. The system of any clause herein, wherein the manipulation instruction is transmitted in real-time or near real-time; and wherein the slave pressure system is activated in real-time or near real-time.

Clause 99. The system of any clause herein, wherein the master device comprises at least one of a glove device, a joystick, and a model of the treatment device.

Clause 100. The system of any clause herein, wherein the treatment device comprises at least one of a physical therapy device, a brace, a mat, and a wrap.

Clause 101. The system of any clause herein, further comprising:

a master memory device operatively coupled to the master processing device, wherein the master memory device stores master instructions, and wherein the master processing device is configured to execute the master instructions; and a slave memory device operatively coupled to the slave processing device, wherein the slave memory device stores slave instructions, and wherein the slave processing device is configured to execute the slave instructions.

Clause 102. A method for operating a remote examination of a patient, comprising:

causing a master processing device to:
receive slave sensor data from the slave processing device;
use a manipulation of a master device to generate a manipulation instruction; and
transmit the manipulation instruction to the slave processing device; and causing a slave processing device to:
receive the slave sensor data from the one or more slave sensors;
transmit the slave sensor data to the master processing device;
receive the manipulation instruction from the master processing device; and
use the manipulation instruction to activate the slave pressure system.

Clause 103. The method of any clause herein, wherein the master device comprises master sensors for detecting master sensor data correlating with the manipulation; and wherein the manipulation instruction is based on the master sensor data.

Clause 104. The method of any clause herein, wherein the slave sensor data comprises slave force measurements;

wherein the master device comprises a master pressure system; and causing the master processing device, based on the slave force measurements, to activate the master pressure system.

Clause 105. The method of any clause herein, further comprising:

a second master device comprising a second master pressure system;

wherein the slave sensor data comprises slave force measurements; and wherein, using the slave force measurements, the master processing device is further configured to activate the second master pressure system.

Clause 106. The method of any clause herein, further causing the master processing device to:

use the slave sensor data to transmit an augmented image to a master display.

Clause 107. The method of any clause herein, wherein the slave sensor data comprises slave force measurements;

wherein the augmented image comprises one or more pressure indicators; and wherein the one or more pressure indicators are based on the slave force measurements.

Clause 108. The method of any clause herein, wherein the slave sensor data comprises slave temperature measurements;

wherein the augmented image comprises one or more temperature indicators; and wherein the one or more temperature indicators are based on the slave temperature measurements.

Clause 109. The method of any clause herein, wherein the master device comprises a pressure gradient; and wherein, using the pressure gradient, activating the slave pressure system comprises applying one or more measured levels of force to one or more sections of the treatment device.

Clause 110. The method of any clause herein, wherein the augmented image comprises a representation of at least one of the treatment device and a body part of the patient, and wherein the representation is in 2D or 3D.

Clause 111. The method of any clause herein, wherein the manipulation instruction comprises a measured level of force; and wherein the measured level of force is based on a proximity of the master device to the representation.

Clause 112. The method of any clause herein, wherein the manipulation instruction is transmitted in real-time or near real-time; and wherein the slave pressure system is activated in real-time or near real-time.

Clause 113. The method of any clause herein, wherein the master device comprises at least one of a glove device, a joystick, and a model of the treatment device.

Clause 114. The method of any clause herein, wherein the treatment device comprises at least one of a physical therapy device, a brace, a mat, and a wrap.

Clause 115. A tangible, non-transitory computer-readable storage medium storing instructions that, when executed, cause a master processing device to:
receive slave sensor data from the slave processing device;
use a manipulation of a master device to generate a manipulation instruction; and
transmit the manipulation instruction to the slave processing device; and cause a slave processing device to:
receive the slave sensor data from the one or more slave sensors;
transmit the slave sensor data to the master processing device;

receive the manipulation instruction from the master processing device; and use the manipulation instruction to activate the slave pressure system.

Clause 116. The tangible, non-transitory computer-readable storage medium of any clause herein, wherein the master device comprises master sensors for detecting master sensor data correlating with the manipulation; and wherein the manipulation instruction is based on the master sensor data.

Clause 117. The tangible, non-transitory computer-readable storage medium of any clause herein, wherein the slave sensor data comprises slave force measurements;

wherein the master device comprises a master pressure system; and wherein, using the slave force measurements, the master processing device is further configured to activate the master pressure system.

Clause 118. The tangible, non-transitory computer-readable storage medium of any clause herein, further comprising:

a second master device comprising a second master pressure system;

wherein the slave sensor data comprises slave force measurements; and wherein, using the slave force measurements, the master processing device is further configured to activate the second master pressure system.

Clause 119. The tangible, non-transitory computer-readable storage medium of any clause herein, wherein instructions further cause the master processing device to:

use the slave sensor data to transmit an augmented image to a master display.

Clause 120. The tangible, non-transitory computer-readable storage medium of any clause herein, wherein the slave sensor data comprises slave force measurements;

wherein the augmented image comprises one or more pressure indicators; and wherein the one or more pressure indicators are based on the slave force measurements.

Clause 121. The tangible, non-transitory computer-readable storage medium of any clause herein, wherein the slave sensor data comprises slave temperature measurements;

wherein the augmented image comprises one or more temperature indicators; and wherein the one or more temperature indicators are based on the slave temperature measurements.

Clause 122. The tangible, non-transitory computer-readable storage medium of any clause herein, wherein the master device comprises a pressure gradient; and wherein, using the pressure gradient, activating the slave pressure system comprises applying one or more measured levels of force to one or more sections of the treatment device.

Clause 123. The tangible, non-transitory computer-readable storage medium of any clause herein, wherein the augmented image comprises a representation of at least one of the treatment device and a body part of the patient, and wherein the representation is in 2D or 3D.

Clause 124. The tangible, non-transitory computer-readable storage medium of any clause herein, wherein the manipulation instruction comprises a measured level of force; and wherein the measured level of force is based on a proximity of the master device to the representation.

Clause 125. The tangible, non-transitory computer-readable storage medium of any clause herein, wherein the manipulation instruction is transmitted in real-time or near real-time; and wherein the slave pressure system is activated in real-time or near real-time.

Clause 126. The tangible, non-transitory computer-readable storage medium of any clause herein, wherein the master device comprises at least one of a glove device, a joystick, and a model of the treatment device.

Clause 127. The tangible, non-transitory computer-readable storage medium of any clause herein, wherein the treatment device comprises at least one of a physical therapy device, a brace, a mat, and a wrap.

Clause 128. The tangible, non-transitory computer-readable storage medium of any clause herein, further comprising:

a master memory device operatively coupled to the master processing device, wherein the master memory device stores master instructions, and wherein the master processing device is configured to execute the master instructions; and a slave memory device operatively coupled to the slave processing device, wherein the slave memory device stores slave instructions, and wherein the slave processing device is configured to execute the slave instructions.

Consistent with the above disclosure, the examples of assemblies enumerated in the following clauses are specifically contemplated and are intended as a non-limiting set of examples.

No part of the description in this application should be read as implying that any particular element, step, or function is an essential element that must be included in the claim scope. The scope of patented subject matter is defined only by the claims. Moreover, none of the claims is intended to invoke 25 U.S.C. § 104(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A computer-implemented system, comprising:
   a computing device comprising one or more slave sensors and a slave pressure system, the computing device configured to be manipulated by a user;
   a master console comprising a master glove device; and
   a control system comprising one or more processing devices operatively coupled to the master console and the computing device, wherein the one or more processing devices are configured to:
   receive slave sensor data from the one or more slave sensors;

use a manipulation of the master glove device to generate a manipulation instruction;

transmit the manipulation instruction; and use the manipulation instruction to cause the slave pressure system to activate.

2. The computer-implemented system of claim 1, further comprising a user interface comprising an output device configured to present telemedicine information associated with a telemedicine session.

3. The computer-implemented system of claim 2, wherein the one or more processing devices are configured to, during the telemedicine session, use the manipulation instruction to cause the slave pressure system to activate.

4. The computer-implemented system of claim 1, wherein the slave sensor data comprises slave force measurements;

wherein the master glove device comprises a master pressure system; and wherein, using the slave force measurements, the one or more processing devices are further configured to activate the master pressure system.

5. The computer-implemented system of claim 1, wherein the master glove device comprises a pressure gradient.

6. The computer-implemented system of claim 5, wherein, using the pressure gradient, the one or more processing devices are configured to cause the slave pressure system to apply one or more measured levels of force to one or more sections of the computing device.

7. The computer-implemented system of claim 1, wherein the computing device comprises at least one of a glove, a physical therapy device, a brace, a mat, and a wrap.

8. A computer-implemented method comprising:

receive, via one or more processing devices of a control system, slave sensor data from one or more slave sensors, wherein a computing device comprises the one or more slave sensors and a slave pressure system, the one or more processing devices are operatively coupled to a master console and the computing device, and the computing device configured to be manipulated by a user;

use a manipulation of a master glove device to generate a manipulation instruction, wherein the master console comprises the master glove device;

transmit, via the one or more processing devices, the manipulation instruction; and use the manipulation instruction to cause the slave pressure system to activate.

9. The computer-implemented method of claim 8, wherein a user interface comprises an output device configured to present telemedicine information associated with a telemedicine session.

10. The computer-implemented method of claim 9, wherein the one or more processing devices are configured to, during the telemedicine session, use the manipulation instruction to cause the slave pressure system to activate.

11. The computer-implemented method of claim 8, wherein the slave sensor data comprises slave force measurements;

wherein the master glove device comprises a master pressure system; and wherein, using the slave force measurements, the one or more processing devices are further configured to activate the master pressure system.

12. The computer-implemented method of claim 8, wherein the master glove device comprises a pressure gradient.

13. The computer-implemented method of claim 12, wherein, using the pressure gradient, the one or more processing devices are configured to cause the slave pressure system to apply one or more measured levels of force to one or more sections of the computing device.

14. The computer-implemented method of claim 8, wherein the computing device comprises at least one of a glove, a physical therapy device, a brace, a mat, and a wrap.

15. A tangible, non-transitory computer-readable medium storing instructions that, when executed, cause a processing device of a control system to:

receive slave sensor data from one or more slave sensors, wherein a computing device comprises the one or more slave sensors and a slave pressure system, the one or more processing devices are operatively coupled to a master console and the computing device, and the computing device configured to be manipulated by a user;

use a manipulation of a master glove device to generate a manipulation instruction, wherein the master console comprises the master glove device;

transmit the manipulation instruction; and use the manipulation instruction to cause the slave pressure system to activate.

16. The computer-readable medium of claim 15, wherein a user interface comprises an output device configured to present telemedicine information associated with a telemedicine session.

17. The computer-readable medium of claim 16, wherein the processing device is configured to, during the telemedicine session, use the manipulation instruction to cause the slave pressure system to activate.

18. The computer-readable medium of claim 15, wherein the slave sensor data comprises slave force measurements;

wherein the master glove device comprises a master pressure system; and wherein, using the slave force measurements, the processing device is further configured to activate the master pressure system.

19. The computer-readable medium of claim 15, wherein the master glove device comprises a pressure gradient.

20. The computer-readable medium of claim 19, wherein, using the pressure gradient, the processing device is configured to cause the slave pressure system to apply one or more measured levels of force to one or more sections of the computing device.

* * * * *